United States Patent [19]
Panescu et al.

[11] Patent Number: 5,941,251
[45] Date of Patent: *Aug. 24, 1999

[54] SYSTEMS FOR LOCATING AND GUIDING OPERATIVE ELEMENTS WITHIN INTERIOR BODY REGIONS

[75] Inventors: Dorin Panescu, Sunnyvale; James G Whayne, Saratoga; David K Swanson, Mountain View; David McGee, Sunnyvale; David F. Dueiri, Santa Clara, all of Calif.

[73] Assignee: EP Technologies, Inc., Sunnyvale, Calif.

[*] Notice: This patent is subject to a terminal disclaimer.

[21] Appl. No.: 08/745,795

[22] Filed: Nov. 8, 1996

Related U.S. Application Data

[63] Continuation-in-part of application No. 08/679,156, Jul. 12, 1996, Pat. No. 5,722,402, and a continuation-in-part of application No. 08/739,508, Oct. 28, 1996, Pat. No. 5,740,808, said application No. 08/679,156, is a continuation of application No. 08/320,301, Oct. 11, 1994, abandoned.

[51] Int. Cl.⁶ ........................................ A61B 5/00
[52] U.S. Cl. .................... 128/899; 600/374; 606/34; 606/41; 607/122
[58] Field of Search .............. 600/374; 606/34, 606/41; 128/899; 607/122

[56] References Cited

U.S. PATENT DOCUMENTS

| | | |
|---|---|---|
| 4,522,212 | 6/1985 | Gelinas et al. . |
| 4,628,937 | 12/1986 | Hess et al. . |
| 4,649,924 | 3/1987 | Taccardi . |
| 4,674,518 | 6/1987 | Salo . |
| 4,699,147 | 10/1987 | Chilson et al. . |
| 4,852,580 | 8/1989 | Wood . |
| 5,058,583 | 10/1991 | Geddes et al. . |
| 5,092,339 | 3/1992 | Geddes et al. . |
| 5,156,151 | 10/1992 | Imran . |
| 5,282,840 | 2/1994 | Hudrlik . |
| 5,297,549 | 3/1994 | Beatty et al. . |
| 5,309,910 | 5/1994 | Edwards et al. . |
| 5,311,873 | 5/1994 | Savard et al. . |
| 5,323,781 | 6/1994 | Ideker et al. . |
| 5,324,234 | 6/1994 | Imran . |
| 5,327,889 | 7/1994 | Imran . |
| 5,341,807 | 8/1994 | Nardella . |
| 5,383,917 | 1/1995 | Desai et al. . |
| 5,391,199 | 2/1995 | Ben-Haim . |
| 5,409,000 | 4/1995 | Imran . |
| 5,411,025 | 5/1995 | Webster, Jr. . |
| 5,433,198 | 7/1995 | Desai . |
| 5,450,846 | 9/1995 | Goldreyer . |
| 5,465,717 | 11/1995 | Imran et al. . |
| 5,476,495 | 12/1995 | Kordis et al. . |
| 5,487,391 | 1/1996 | Panescu . |
| 5,697,377 | 12/1997 | Wittkampf .............................. 128/899 |
| 5,722,402 | 3/1998 | Swanson et al. ........................ 600/374 |

FOREIGN PATENT DOCUMENTS

| | | |
|---|---|---|
| 0 399 536 A1 | 11/1990 | European Pat. Off. . |
| 0 659 388 A1 | 12/1993 | European Pat. Off. . |

*Primary Examiner*—Lee Cohen
*Attorney, Agent, or Firm*—Lyon & Lyon LLP

[57] ABSTRACT

Systems and methods for locating an operative element within an interior body space use a locating probe, which includes at least one transmitting element to transmit an electric waveform output within at least a portion of the space. The systems and methods also use a sensing element, which is adapted to be carried by the operative element to sense a local electric waveform within the space. A processing element coupled to the sensing element generates a processed output that locates the sensing element relative to the locating probe based, at least in part, upon a differential comparison of the waveform output and the sensed local waveform.

9 Claims, 17 Drawing Sheets

SYSTEMS FOR LOCATING AND GUIDING OPERATIVE ELEMENTS WITHIN INTERIOR BODY REGIONS

RELATED APPLICATION

This application is a continuation-in-part of patent application Ser. No. 08/679,156, filed Jul. 12, 1996 (now U.S. Pat. No. 5,722,402) and entitled "Systems and Methods for Guiding Movable Electrode Elements Within Multiple Electrode Structures," which is a continuation of patent application Ser. No. 08/320,301, filed Oct. 11, 1994 (now abandoned) and entitled "Systems and Methods for Guiding Movable Electrode Elements Within Multiple Electrode Structures". This application is also a continuation-in-part of application Ser. No. 08/739,508, filed Oct. 28, 1996 (now U.S. Pat. No. 5,740,808) and entitled "Systems and Methods for Guiding Diagnostic or Therapeutic Devices in Interior Tissue Regions."

FIELD OF THE INVENTION

The invention generally relates to systems and methods for guiding or locating diagnostic or therapeutic elements in interior regions of the body.

BACKGROUND OF THE INVENTION

Physicians make use of catheters today in medical procedures to gain access into interior regions of the body for diagnostic and therapeutic purposes. It is important for the physician to be able to reliably and precisely position in proximity to desired tissue locations. For example, the need for precise control over the catheter is especially critical during procedures that ablate myocardial tissue from within the heart. These procedures, called ablation therapy, are used to treat cardiac rhythm disturbances.

SUMMARY OF THE INVENTION

This invention has as its principal objective the realization of safe and efficacious systems and methods for remotely locating operative elements at precise locations within the body.

The invention provides systems and methods for locating an operative element within an interior body space. The systems and methods cause a locating probe, which includes at least one transmitting element to transmit an electric waveform output within at least a portion of the space. The systems and methods also use a sensing element, which is adapted to be carried by the operative element to sense a local electric waveform within the space. A processing element coupled to the sensing element generates a processed output that locates the sensing element relative to the locating probe based, at least in part, upon a differential comparison of the waveform output and the sensed local waveform.

Other features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. Differential Waveform Analysis

A. Single Locating Probe

Figure 1:
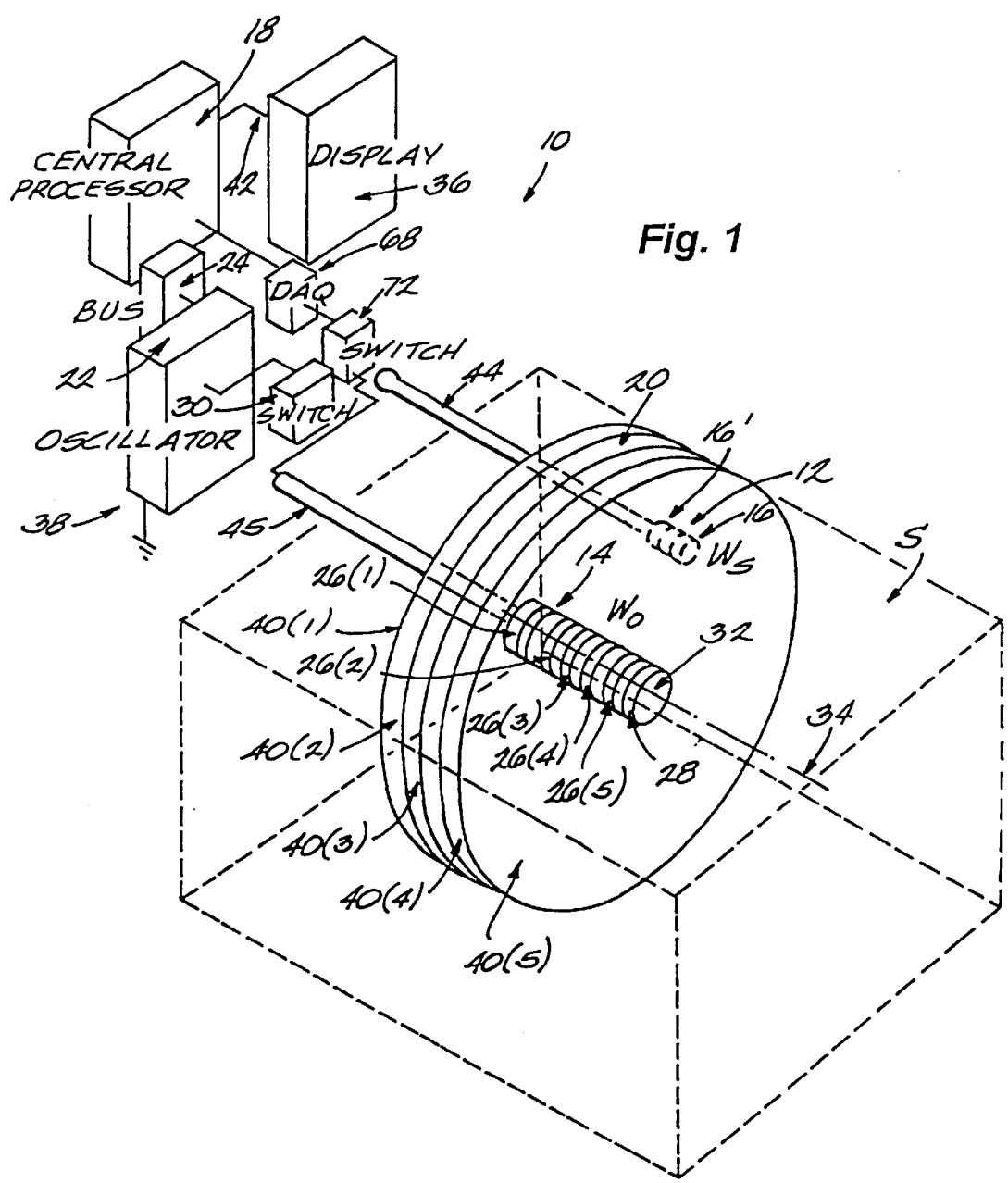
FIG. 1 is a perspective view, somewhat diagrammatic in form, of a system to locate the position of an operative element within a space by generating a waveform energy field from a single locating probe.

FIG. 1 shows a system 10, which locates the position of an operative element 12 within a space (designated S). The system 10 is well adapted for use inside body lumens, chambers or cavities for either diagnostic or therapeutic purposes. For this reason, the system 10 will be described in the context of its use within a living body. The system 10 particularly lends itself to catheter-based procedures, where access to the interior body region is obtained, for example, through the vascular system or alimentary canal, without complex, invasive surgical procedures.

For example, the system 10 can be used during the diagnosis and treatment of arrhythmia conditions within the heart, such as ventricular tachycardia or atrial fibrillation. The system 10 also can be used during the diagnosis or treatment of intravascular ailments, in association, for example, with angioplasty or atherectomy techniques. The system 10 also can be used during the diagnosis or treatment of ailments in the gastrointestinal tract, the prostate, brain, gall bladder, uterus, and other regions of the body.

For deployment into an interior body space S, the operative element 12 is carried in the illustrated embodiment at the distal end of a catheter tube 44. Nevertheless, the system 10 can also be used in association with systems and methods that are not necessarily catheter-based. The operative element 12 can take different forms and can be used for either therapeutic purposes, or diagnostic purposes, or both. The operative element 12 can comprise, for example, a device for imaging body tissue, such as an ultrasound transducer or an array of ultrasound transducers, or an optic fiber element. Alternatively, the operative element 12 can comprise a device to deliver a drug or therapeutic material to body tissue. Still alternatively, the operative element 12 can comprise a device, e.g., an electrode, for sensing a physiological characteristic in tissue, such as electrical activity in heart tissue, or for transmitting energy to stimulate or ablate tissue.

The system 10 includes a locating probe 14, which, like the operative element 12, is carried at the distal end of a catheter tube 45 for introduction into the body space S. In use, the locating probe 14 establishes a localized field 20 comprising waveform energy in at least a portion of the space S.

The system 10 provides a sensing element 16 on the operative element 12. When located within the energy field 20, the sensing element 16 acquires local characteristics of the energy field 20 surrounding it. The sensing element 16 may be a component added to the operative element 12, or it may comprise a component already on the operative element 12, but used for an additional purpose.

The system 10 further includes a central processing unit 18. The central processing unit 18 receives as input the energy field characteristic acquired by the sensing element 16. The central processing unit 18 derives a position-indicating output 42, which locates the position of the sensing element 16, and thus the operative element 12 itself, relative to the locating probe 14 within the space S.

In the illustrated embodiment, the central processing unit 18 includes an output display device 36 (e.g., a CRT, LED display, or a printer). The device 36 presents the position-indicating output 42 in a visual format useful to the physician for remotely locating and guiding the operative element 12 within the localized energy field 20 generated by the locating probe 14. Further details for processing the position-indicating output 42 for display will be described in greater detail later.

The system 10 includes an oscillator 22, which generates the waveform comprising the energy field 20. In the illustrated embodiment, the central processing unit 18, which is coupled to the oscillator 22 by a control bus 24, conditions the oscillator 22 to generate an electrical alternating current (AC) waveform at a predetermined amplitude and frequency.

For use within a living body space, the selected current amplitude of the oscillator output can vary between 0.1 mAmp to about 5 mAmp. The frequency selected can also vary from about 5 kHz to about 100 kHz. When the space S is adjacent heart tissue, currents substantially above about 5 mAmp and frequencies substantially below 5 kHz should be avoided, as they pose the danger of inducing fibrillation. The maximum current is a function of the frequency, as expressed in the following equation:

$$I = f \times 10$$

where I is current in $\mu$amp, and f is frequency in kHz.

The shape of the waveform can also vary. In the illustrated and preferred embodiment, the waveform is sinusoidal. However, square wave shapes or pulses can also be used, although harmonics may be encountered if capacitive coupling is present. Furthermore, the waveform need not be continuous. The oscillator 22 may generate pulsed waveforms.

The locating probe 14 carries at least one electrode 26(1) capable of transmitting energy and at least one energy return electrode 28 capable of returning the energy to ground. These electrodes 26(1) and 28 are electrically coupled to the oscillator 22 through an electronic switch unit 30. The locating probe 14 also carries at least one sensing electrode (four such electrodes 26(2) to 26(5) are shown in FIG. 1), which are located between the transmitting electrode 26(1) and the return electrode 28. Preferably, the sensing electrode(s) 26(2) to 26(5) are also capable of becoming a transmitting electrode in place of the electrode 26(1), to change the point of energy transmission, if desired.

For purposes of description, the illustrated embodiment shows the one return electrode 28 carried at the distal region 32 of the locating probe 14 and the other five electrodes 26(1) to 26(5) carried in a spaced-apart relationship along the probe axis 34, proximal of the return electrode 28, with the transmitting electrode 26(1) being the most proximal.

The number and placement of the electrode(s) 26 and return electrode(s) 28 on the locating probe 14 can vary. Generally speaking, the position-resolution capability of the system 10 improves with increased number of electrodes 26. Also generally speaking, the position-resolution capability of the system 10 improves as the spacing between adjacent intermediate electrodes 26(2) to 26 (5) and the spacing between the transmitting electrode 26(1) and the return electrode 28 decreases.

The geometry of the locating probe 14 itself can also vary. In the illustrated embodiment, the locating probe 14 takes the elongated, cylindrical form of a conventional diagnostic catheter, which is well suited for deployment in interior body regions.

In the illustrated embodiment, the central processing unit 18 is capable of connecting the waveform output of the oscillator 22 through the switch unit 30 between the transmitting electrode 26(1) and the return electrode 28, which is coupled to isolated ground or patient ground 38. This creates an energy waveform field 20 emanating into at least a portion of the space S.

The central processing unit 18 is also capable of acquiring a differential voltage between electrodes 26(1) to 26 (5) and the sensing electrode 16 through another switch element 72 and a data acquisition element DAQ 68. The differential voltage measurements are taken along iso-potential surfaces 40(1) to 40(5) in the energy waveform field 20.

Figure 2:
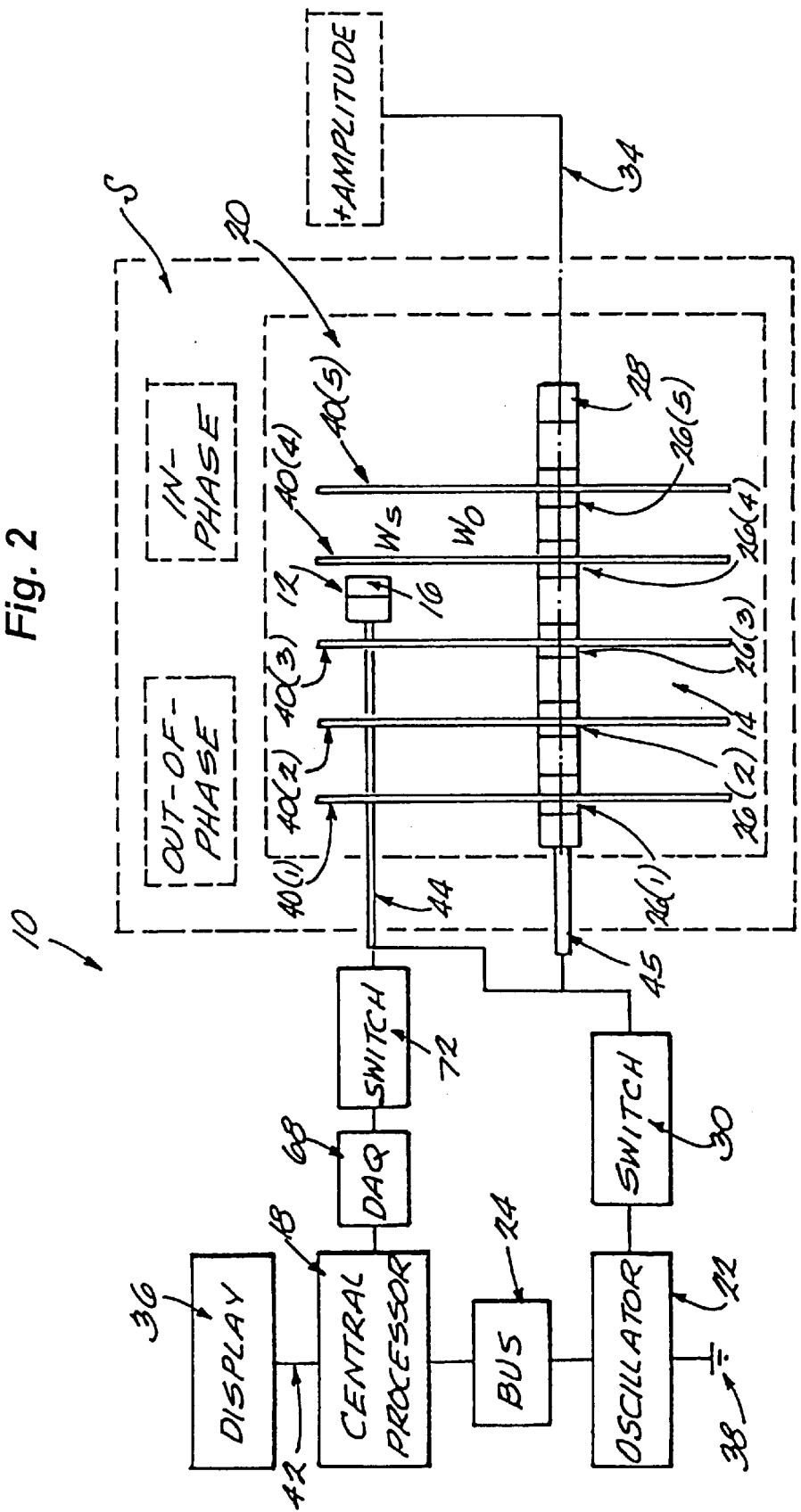
FIG. 2 is a diagrammatic plan view of the system shown in FIG. 1, showing a representative position of the operative element relative to waveform phase iso-potential surfaces generated within the space.

FIG. 1 shows the iso-potential surfaces associated with electrodes 26(1), 26(2), 26(3), 26(4), and 26(5) as, respectively, planes 40(1), 40(2), 40(3), 40(4), and 40(5). FIG. 2 shows the energy field 20 and the iso-potential surfaces 40(1) to 40(5) in plan view.

For the purpose of illustration, the iso-potential surfaces 40 are shown as planar surfaces or planes. Actually, the iso-potential surfaces typically will take the form of more complex, closed curvilinear surfaces, which are orthogonal to the probe axis 34 near the probe, but which deviate significantly from planar with increasing distance from the probe. The depiction of the surfaces 40 in the drawings aids in the understanding of the invention, as coordinate locations in and intersections of the more complex iso-potential surfaces 40 can generally be treated equivalent to coordinate locations and intersections of planar surfaces.

As FIG. 2 shows, the differential comparison along the iso-potential surfaces 40(1) to 40(5) derives either an in-phase relationship or an out-of-phase relationship between the voltage sensed by the element 16 ($W_S$) and the voltage at the plane of the sensing electrode ($W_O$), depending upon the location of the sensing element 16 relative to the iso-potential surface 40 of the electrode 26 along which the differential measurement is acquired.

More particularly, FIG. 2 shows the sensing element 16 to be located to the right of iso-potential surfaces 40(1), 40(2), and 40(3) and to the left of the iso-potential surfaces 40(4) and 40(5). In this orientation, when either surface 40(1) or 40(2) or 40(3) is the surface along which the differential measurement is taken, the differential comparison of $W_S$ and $W_O$ indicates an out-of-phase relationship between the two waveforms. The out-of-phase relationship indicates that the iso-potential surfaces 40(1), 40(2), or 40(3) are located in a proximal direction relative to the sensing element 16, meaning that the sensing element 16 is located between these iso-potential surfaces and the return electrode 28.

Conversely, when the differential measurement is acquired along either surface 40(4) or 40(5), the differential comparison of $W_S$ and $W_O$ indicates an in-phase relationship between the two waveforms. The in-phase relationship indicates that the iso-potential surfaces 40(4) or 40(5) are located in a distal direction relative to the sensing element 16, meaning that the these iso-potential surfaces are located between the sensing element 16 and the return electrode 28.

The central processing unit 18 controls the switch unit 72 to electronically switch the electrodes 26(2) to 26(5) to perform a differential comparison of the waveform $W_S$ of the sensing electrode 16 and the waveform $W_O$ of the switched-on electrode 26. In FIG. 2, the differential comparison of $W_S$ and $W_O$ will shift from an out-of-phase condition to an in-phase condition when the measurement is acquired along the iso-potential surface 40(4). The switch point between out-of-phase and in-phase conditions marks the longitudinal orientation of the sensing element 16 (and thus the operative element 12) along the axis 34 of the locating probe 14, i.e., between iso-potential surface 40(3) and iso-potential surface 40(4).

The central processing unit 18 can also perform a differential comparison between the signal amplitude of the acquired waveform $A_S$ and the signal amplitude of the waveform $A_O$ at the switched-on sensing electrode 26. From the differential amplitude comparison, the central processing unit 18 derives the latitudinal orientation of the operative element 12 perpendicular to the axis 34 of the locating probe 14, i.e., the vertical distance within the space S between the operative element 12 and the probe axis 34. The magnitude of the difference between $A_S$ and $A_O$ increases as a function of increasing distance between the sensing element 16 and the plane of the switched-on electrode 26. The function governing the increase of the amplitude differential over distance can be empirically determined, or be determined by finite element analysis.

Figure 3:
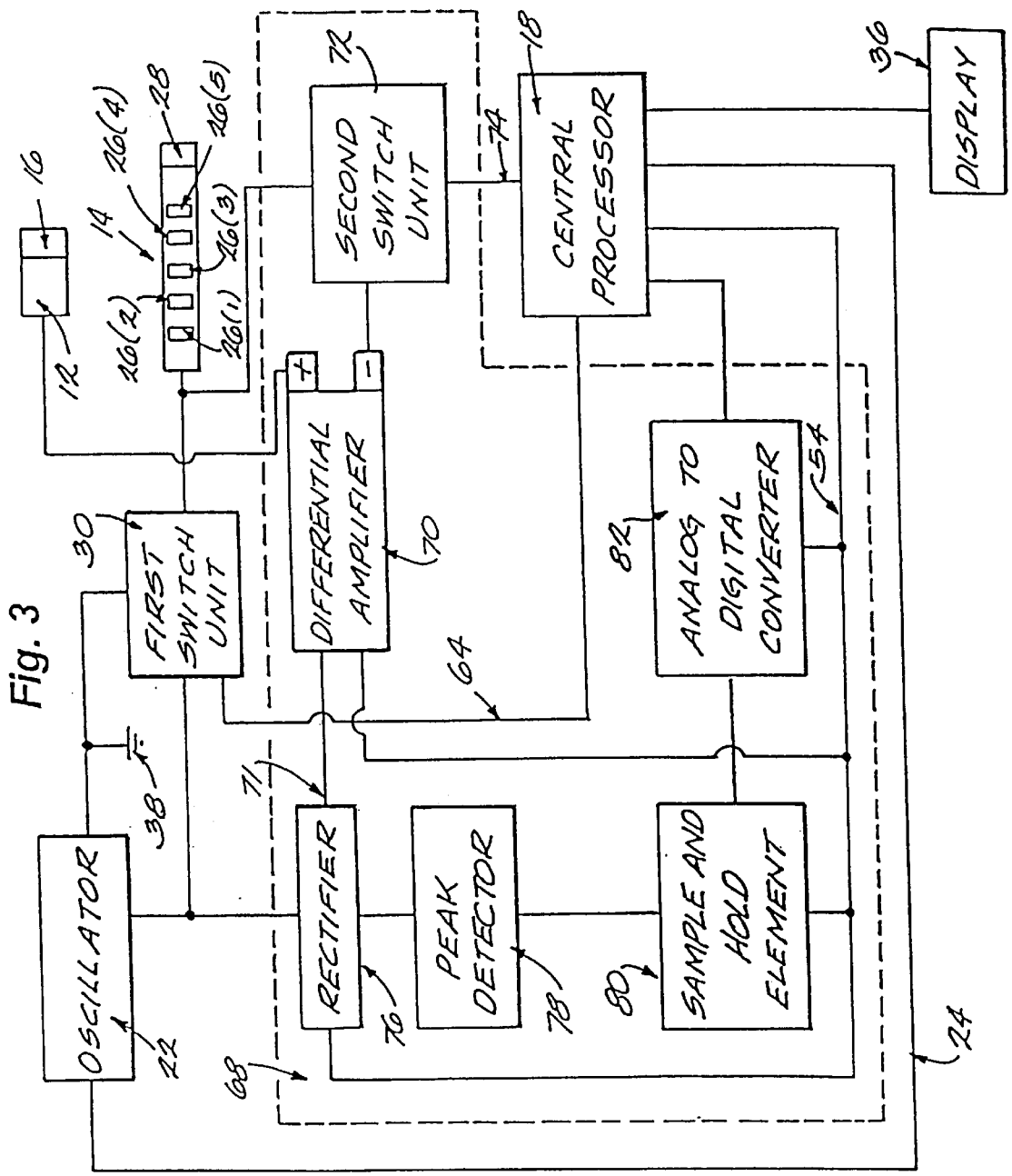
FIG. 3 is a schematic view of an assembly of electrical components that the system shown in FIG. 1 can employ in carrying out its locating functions.

There are various electrical configurations, analog or digital, that can be used to carry out the above differential comparisons. FIG. 3 shows one representative implementation.

In FIG. 3, the system 10 includes an address bus 64, which couples the central processing unit 18 to the first-described switch unit 30. The first switch unit 30 is also coupled to a transmitting electrode, e.g. electrode 26(1), and return electrode 28. The central processing unit 18 conditions the first switch unit 30 via the bus 64 to distribute the alternating current output of the oscillator 22 in a prescribed fashion in parallel to at least the electrodes 26 (1) for return through the return electrode 28.

In this arrangement, the system 10 also includes a data acquisition system (DAQ) 68. The DAQ 68 includes a differential amplifier 70. The sensing element 16 is coupled to the noninverting (+) input of the amplifier 70.

The DAQ 68 further includes the second electronic switch unit 72, which is independently coupled to the electrodes 26(1) to 26(5). The central processing unit 18 conditions the second switch unit 72 via a second address bus 74 to couple a selected one transmitting electrode 26 on the locating probe 14 to the inverting (−) input of the amplifier 70.

In this arrangement, the differential amplifier 70 reads the electrical potential of the sensing element 16 with respect to that of the switched-on transmitting electrode 26, then coupled to the amplifier 70 by the switch unit 72. The output 71 of the amplifier 70 is an AC voltage signal.

The DAQ 68 also includes a synchronized rectifier 76 and peak detector 78. The rectifier 76 receives the AC signal voltage output of the amplifier 70 and acquires its phase relative to the phase at the output of the oscillator 22. The detector 78 determines the peak amplitude of the AC voltage signal output 71 of the amplifier 70. In an alternative implementation, the rectifier 76 and detector 78 can take the form of a synchronized phase detector, or any other element that detects phase and amplitude (whether as an RMS value, peak value, average rectified value, or otherwise).

The output of the detector 78 is an analog signal having a value corresponding to the peak amplitude of the AC output of the amplifier 70, and a sign (+ or −) denoting whether the AC voltage output is in phase with the oscillator 22 (+) or out of phase with the oscillator 22 (−).

The DAQ 68 registers this analog signal in association with the switched-on electrode 26 then-coupled to the amplifier 70 in a sample and hold element 80. An analog to digital converter 82 converts the analog signals to digital signals for processing by the central processing unit 18. A suitable control bus 54 couples the sample and hold element 80, converter 82, and differential amplifier 70 to the central processing unit 18 for coordination and control functions. For example, the central processing unit 18 can set the sampling rate of the sample and hold element 80, the input range of the converter 82, and the amplification of the amplifier 70.

In determining the longitudinal location of the sensing element 16, the central processing unit 18 conditions the first switch unit 30 to connect the return electrode 28 to the isolated ground 38 of the oscillator 22.

The central processing unit 18 also conditions the first switch element 30 to direct AC current flow from the oscillator 22 in parallel to the most proximal transmitting electrode 26(1), while also conditioning the second switch unit 72 to couple the switched-on transmitting electrode 26(1) to the inverting input of the differential amplifier 70. The amplifier 70 subtracts the electrical potential measured at the switched-on electrode 26(1) from the electrical potential measured by the sensing element 16. The differential potential times the gain of the amplifier 70 constitutes the input to the rectifier 76.

The rectifier 76 senses the synchronization of the phase of its input voltage relative to the phase of the oscillator 22, while the detector 78 senses the peak voltage. This signed analog value is passed through the sample and hold element 80, converted to a digital format by the converter 82 and registered by the central processing unit 18 in association with the identity of the switched-on transmitting electrode 26(1).

The central processing unit 18 next conditions the second switch unit 72 to couple the electrode 26(2) to the inverting input of the differential amplifier 70. The central processing unit 18 processes the signal obtained for the switched-on electrode 26(2) in the same fashion as the output voltage signal for the first switched-on electrode 26(1). The central processing unit 18 proceeds in like fashion sequentially through all the remaining electrodes 26(3), 26(4), and 26(5), deriving and processing the output voltage signal for each switched-on electrode 26. The processor 18 registers the digitally converted peak voltages and phase synchronization for each switched-on transmitting electrode 26(1) to 26(5).

Typically, it can be expected that the electrical capacitances and inductances of tissue in and about the space S are minimal. Therefore, the synchronization of the phase of the output voltage signal of the amplifier 70 relative to the phase of the oscillator 22 will vary depending upon whether the sensing element 16 is located to the left or to the right of the transmitting electrode 26 then-coupled to the inverting input of the amplifier 70 (as FIG. 2 shows).

If the switched-on electrode 26 is located to the left of the sensing element 16 (as FIG. 2 shows for electrodes 26(1), 26(2), and 26(3)), the output voltage signal of the amplifier 70 will be out of phase with respect to the phase of the oscillator 22 (i.e., that analog signal received by the sample and hold element 80 will have a (−) sign). This is because the potential of the sensing element 16 acquired at the noninverting input of the amplifier 70 (during the positive phase of oscillator output) will be more negative than the potential acquired at the electrodes 26(1), 26(2), and 26(3), which are sensed at the inverting input of the amplifier 70. As long as the potential of the sensing element 16 remains more negative under these conditions, the output voltage signal of the amplifier 70 remains negative, indicating an out of phase condition.

If the switched-on electrode 26 is located to the right of the sensing element 16, (as FIG. 2 shows for transmitting electrode 26(4) and 26(5)), the output voltage signal of the amplifier 70 will be in phase with respect to the phase of the oscillator 22. This is because the potential of the sensing element 16 acquired at the noninverting input of the amplifier 70 (during the positive phase of oscillator output) will be more positive than the potential at the electrodes 26(4) and 26(5) sensed at the inverting input of the amplifier 70. As long as the potential of the sensing element 16 remains more positive under these conditions, the output voltage signal of the amplifier 70 remains positive, indicating an in phase condition.

The central processing unit 18 monitors the output of the peak detector 78 to determine where the output changes sign, by turning from (−) to (+) or vice versa. In FIG. 2, this transition occurs between switched-on electrode 26(3) and switched-on electrode 26(4). The iso-potential surface 40(3) associated with the electrode 26(3) sets the longitudinal coordinate of the sensing element 16, and thus the operative element 12.

To determine the latitudinal coordinate of the sensing element 16 using differential amplitude sensing, the central processing unit 18 conditions the first switch unit 30 to direct AC current flow from the oscillator 22 to the particular switched-on electrode 26(3) at which the phase transition occurred. The central processing unit 18 conditions the second switch unit 72 to couple the particular phase transition electrode 26(3) to the inverting input of the differential amplifier 70 while sensing element 16 is coupled to the noninverting input of the amplifier 70. The amplifier subtracts the electrical potential measured at the phase-transition electrode 26(3) from the electrical potential measured at the sensing element 16. The differential potential times the gain of the amplifier 70 constitutes the input to the rectifier 76.

The detector 78 senses the peak voltage amplitude of the signal. The output of the peak detector 78 is passed through the sample and hold element 80 and converted to digital format by the converter 82. This digitally converted peak voltage amplitude is registered by the central processing unit 18. The central processing unit 18 compares the peak voltage amplitude to a voltage amplitude variation table stored in memory, which lists variations in peak voltage amplitude as a function of distance from the plane of the transmitting electrode. The voltage amplitude variation table can be empirically determined or based upon finite element analysis, taking into account the physical and electrical parameters of the space S.

In a preferred embodiment, a predetermined threshold amplitude is established, which corresponds to a nominal distance from the transmitting electrode, which differentiates between a "close condition" (i.e., equal to or less than the nominal distance) and a "far condition" (i.e., greater than the nominal distance). When the sensed peak voltage amplitude is equal to or less than the threshold amplitude, the central processing unit 18 generates an output that notifies the physician of the "close condition" between the sensing element 16 and the switched-on transmitting electrode 26. When the sensed peak voltage amplitude is less than the threshold amplitude, the central processing unit 18 generates an output that notifies the physician of the "far condition"

between the sensing element 16 and the switched-on transmitting electrode 26. In this way, the physician has at least a qualitative indication of the position of the sensing element 16 relative to the switched-on transmitting electrode 26. In one embodiment, the physician can indicate through input to the central processing unit 18 the magnitude of the nominal distance, or, alternatively, establish a range of distances that progressively indicate a "closest", "closer" and "close" variation of positions.

In another embodiment, the sensing of the voltage amplitude is accomplished in a way that also provides information regarding the orientation of the sensing element 16 relative to the switched-on transmitting electrode 26. More particularly, as shown in FIG. 1, the operative element 12 can carry a second sensing element 16' spaced a known distance apart from the first mentioned sensing element 16. In this arrangement, one or more transmitting electrodes on one probe are switched on in sequence or simultaneously to transmit the energy field to an indifferent patch electrode, which serves as a return path. Sensing individually at each sensing element 16 and 16' provides, not only a peak voltage amplitude, but also, through a comparison of relative phases and amplitudes at each element 16 and 16', information regarding the orientation of the operative element 12 itself. For example, the central processing unit 18 can differentially compare the amplitude at sensing element 16' with the amplitude at sensing element 16 to determine that element 16 is further away from the transmitting electrodes than element 16'. This indicates that the orientation of the operative element 12 is skewed within the space S.

In an alternative embodiment, the second sensing element 16' can comprise the return path for the transmitting electrode 26, instead of a return path electrode 28 carried by the locating probe 14. In yet another alternative embodiment, the energy field can be transmitted by one of the elements 16 or 16' and returned by the other one of the element 16' or 16. In either of theses arrangements, the peak voltage amplitude is sensed by an electrode on one of the locating probes.

B. Multiple Locating Probes

Figure 4:
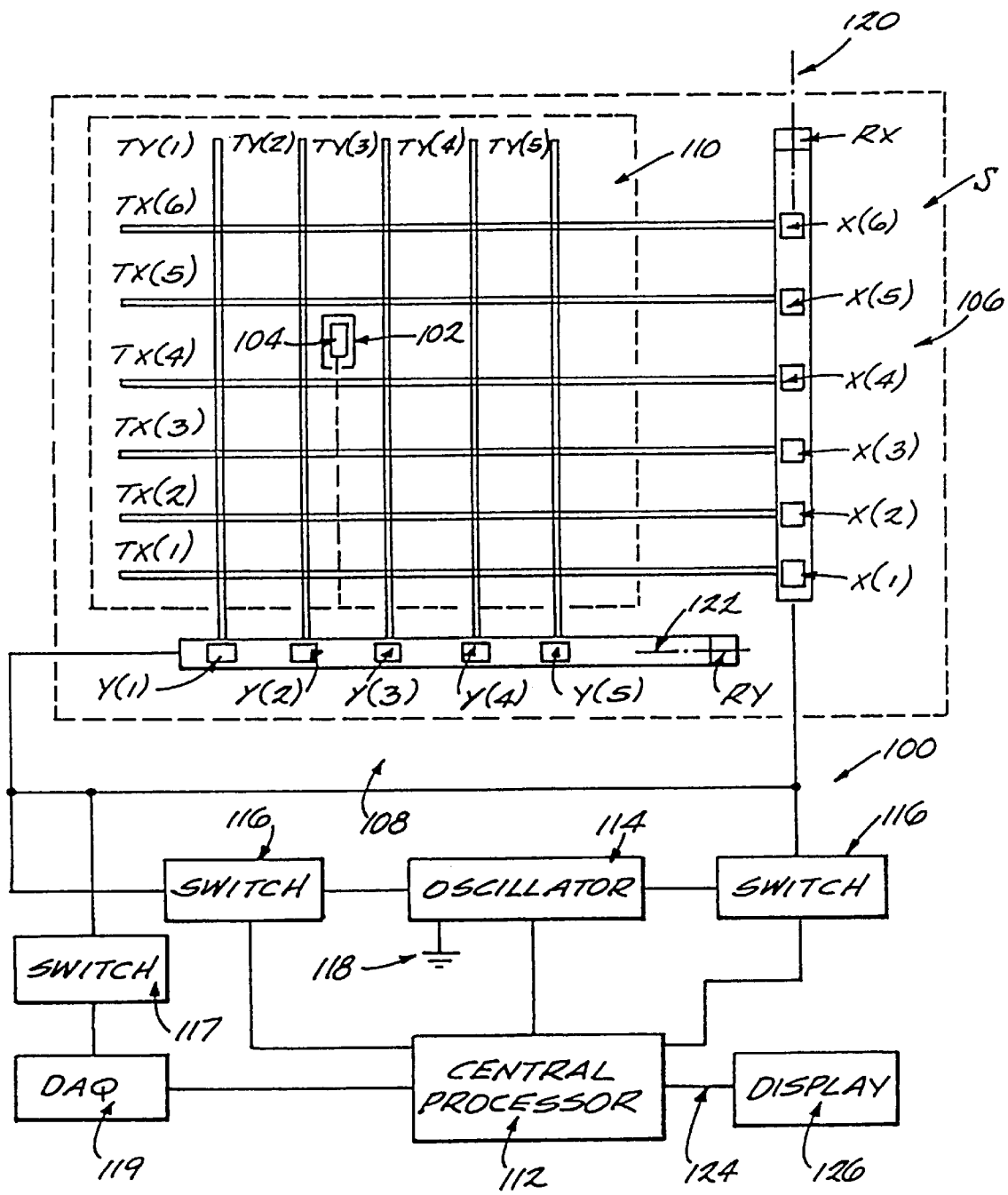
FIG. 4 is a diagrammatic plan view of a system to locate the position of an operative element within a space by generating a waveform energy field from multiple locating probes, showing a representative position of the operative element relative to the intersecting waveform phase iso-potential surfaces generated within the space.
Figure 5:
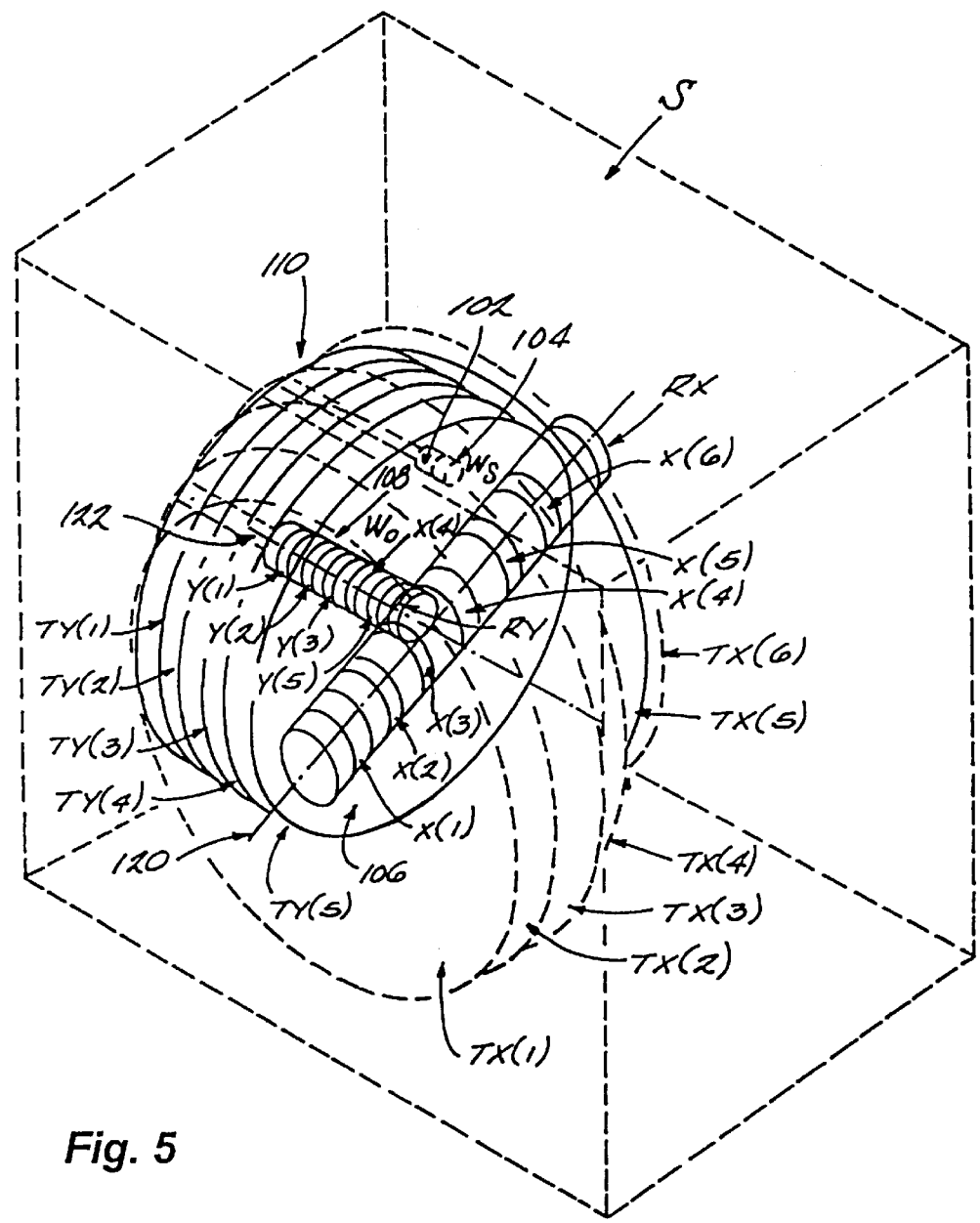
FIG. 5 is a perspective view, somewhat diagrammatic in form, of the system shown in FIG. 4.

FIGS. 4 and 5 show a system 100 that locates an operative element 102 within a space (designated S) by generating an energy waveform field 110 using two locating probes 106 and 108. Each locating probe 106 and 108 is generally like the locating probe 14 shown in FIGS. 1 and 2, having at least one transmitting electrode and at least one return electrode. For purpose of illustration, the locating probes 106 and 108 each carry more electrodes than the probe 14. The electrodes carried by the locating probe 106 are designated X(1) to X(6) and the electrodes carried by the locating probe 108 are designated Y(1) to Y(5). Each locating probe 106 and 108 also includes a return electrode, designated RX for probe 106 and RY for probe 108.

The locating probes 106 and 108 are positioned relative to each other in or near the space, such that their elongated axes, respectively 120 and 122, are not parallel, but extend at an angle. In the illustrated embodiment, the angle is about 90°, but other smaller or larger angles can be used. Furthermore, the locating probes 106 and 108 need not lie in the same plane.

As in the FIGS. 1 and 2 embodiment, the operating element 102 carries a sensing element 104.

Like the system 10 described in FIGS. 1 and 2, the operation of the system 100 is governed by a central processing unit 112. The central processing unit 112 connects the waveform output of an oscillator 114 through a switch unit 116 between the selected transmitting electrode Y(1) and X(1) on the locating probes 106 and 108 and the respective return electrode RY and RX, which is also couple to isolated ground or patient ground 118. The central processing unit 112 also couples the sensing element 104 to the electrodes of the probes 106 and 108 (via the switch unit 117 and DAQ 119) along the iso-potential surfaces TX(1) to TX(6) and TY(1) to TY(5) in the energy waveform field 110. Due to the angular placement of the locating probes 106 and 108, the iso-potential surfaces TX(1) to TX(6) of the probe 106 intersect the iso-potential surfaces TY(1) to TY(5) of the probe 108. FIG. 4 shows the intersecting iso-potential surfaces TX and TY in side view. FIG. 5 shows the intersecting iso-potential surfaces TX and TY in perspective view.

As previously described, the central processing unit 112 performs a differential comparison of the waveform $W_S$ to the waveform output $W_O$ when each of the transmitting electrodes X(1) to X(6) and Y(1) to Y(5) are switched on. The differential comparison derives either an in-phase or relationship an out-of-phase relationship between $W_S$ and $W_O$, depending upon the location of the sensing element 104 relative to the iso-potential surface TX(N) or TY(N) of the switched-on voltage sensing electrode X(N) or Y(N).

More particularly, FIG. 4 shows the sensing element 104 to be located to the right of (or above, in the vertical orientation shown in FIG. 4) the iso-potential surfaces TX(1) to TX(4) and to the left of (or below, from the vertical orientation shown in FIG. 4) the iso-potential surfaces TX(5) and TX(6). In this orientation, when either plane TX(1) or TX(2) or TX(3) or TX(4) is switched-on for sensing, the differential comparison of $W_S$ and $W_O$ indicates an out-of-phase relationship between the two waveforms. This means that the sensing element 104 is located between these planes and the return electrode RX. Conversely, when either plane TX(5) or TX(6) is switched-on for sensing, the differential comparison of $W_S$ and $W_O$ indicates an in-phase relationship between the two waveforms. This means that these planes are located between the sensing electrode 104 and the return electrode RX.

The central processing unit 112 controls the switch unit 116 to electronically switch the electrodes on, sequentially from most proximal to most distal, i.e., sequentially from left to right (or from bottom to top, in the vertical orientation shown in FIG. 4) from X(1) to X(6). This sequentially switches on differential sensing along the iso-potential surfaces TX(1) to TX(6).

For each switched-on electrode X(1) to X(6), the central processing unit 112 performs (via the DAQ 119) a differential comparison of the waveform $W_S$ of the sensing electrode 104 and the waveform $W_O$ of the switched-on electrode X(N). In FIG. 4, the differential comparison of $W_S$ and $W_O$ will shift from an out-of-phase condition to an in-phase condition when measurement occurs along the iso-potential surface TX(5). The switch point between out-of-phase and in-phase conditions marks the longitudinal orientation of the sensing element 104 (and thus the operative element 102) along the axis 120 of the locating probe 106, i.e., between iso-potential surface TX(4) and iso-potential surface TX(5).

The central processing unit 112 can also perform a differential comparison between the signal amplitude of the sensed waveform $A_S$ and the signal amplitude of the waveform at the switched-on transmitting electrode $A_O$. From the differential amplitude comparison, the central processing unit 112 derives the latitudinal orientation of the operative element 102 perpendicular to the axis 120 of the probe 106, i.e., the vertical distance within the space S between the operative element 102 and the probe axis 120.

The same methodology is repeated along the locating probe 108. FIG. 4 shows the sensing element 104 to be located to the right of the iso-potential surfaces TY(1) to TY(2) and to the left of the iso-potential surfaces TY(3), TY(4), and TY(5). The central processing unit 112 controls the switch unit 117 to electronically switch on the transmitting electrodes, sequentially from most proximal to most distal, i.e., sequentially from left to right, Y(1) to Y(5). This sequentially switches on differential sensing along the iso-potential surfaces TY(1) to TY(5).

For each switched-on electrode Y(1) to Y(5), the central processing unit 112 performs (via the DAQ 119) a differential comparison of the waveform $W_S$ of the sensing element 104 and the waveform $W_O$ of the switched-on transmitting electrode Y(N). In FIG. 4, the differential comparison of $W_S$ and $W_O$ along the probe 108 will shift from an out-of-phase condition to an in-phase condition when iso-potential surface TY(3) is switched on. The switch point between out-of-phase and in-phase conditions marks the longitudinal orientation of the sensing element 104 (and thus the operative element 102) along the axis 122 of the locating probe 108, i.e., between iso-potential surface TY(2) and iso-potential surface TY(3).

The central processing unit 112 can also perform a differential comparison between the signal amplitude of the sensed waveform $A_S$ and the signal amplitude of the waveform at the switched-on transmitting electrode $A_O$ to derive the latitudinal orientation of the operative element 102 perpendicular to the axis 122 of the probe 108, i.e., the vertical distance within the space S between the operative element 102 and the probe axis 122.

The component parts of the system 100 can incorporate the particular electrical configuration shown in FIG. 3, or another analog or digital configuration, to carry out the above differential comparisons.

The central processing unit 112 provides a position-indicating output 124, which correlates the position of the sensing element 104 (and thus the operative element 102) within the grid of intersecting iso-potential surfaces TX(N) and TY(N). Preferably, the position-indicating output 124 is presented to the physician on a display device 126.

Figure 6:
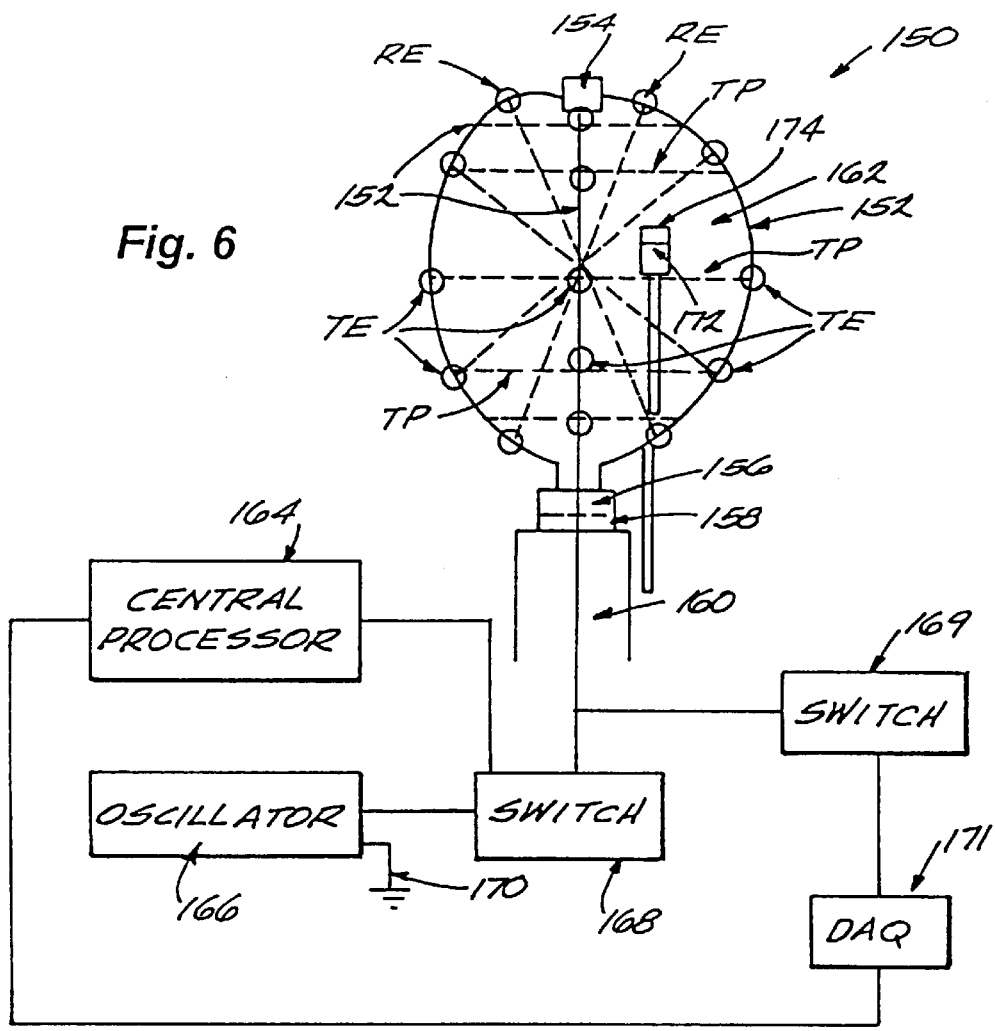
FIG. 6 is a side view of an assemblage of multiple locating probes in a composite structure, which is shown in an expanded condition ready for use.

The individual identification probes 106 and 108 shown in FIGS. 4 and 5 can be assembled into a composite structure 150, as shown in FIG. 6. In this arrangement, the structure 150 comprises an array of flexible spline elements 152 extending longitudinally between a distal hub 154 and a proximal base 156. For purpose of illustration, the structure 150 includes four spline elements 152(1) to 152(4) (only 3 spline elements are visible in FIG. 6). A greater or lesser number of spline elements 152 can be present.

Each spline element 152 preferably comprises a flexible body made from resilient, inert wire or plastic. Elastic memory material such as nickel titanium (commercially available as NITINOL™ material) can be used. Resilient injection molded plastic or stainless steel can also be used. Each spline element 152 is preferably preformed with a convex bias, creating a normally open three-dimensional basket structure.

Figure 7:
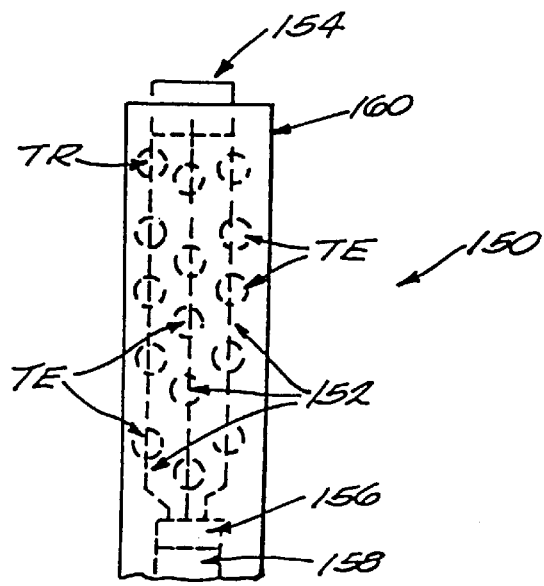
FIG. 7 is the composite locating probe structure shown in FIG. 6, except shown in a collapsed condition for deployment into a body region.

The structure 150 is carried at the end of a catheter tube 158. An outer sheath 160 slidably advances forward along the catheter tube 158 to compress and collapses the structure 150 (see FIG. 7) for introduction into the body region. Rearward movement retracts the slidable sheath 160 away from the structure 150, which springs open and assumes its three-dimensional shape (as FIG. 6 shows).

In FIG. 6, the geometry of spline elements 152 is both radially and axially symmetric. Asymmetric structures, either radially or axially or both, can also be used. Examples of asymmetric arrays of spline structures are shown in copending U.S. application Ser. No. 08/742,569, filed Oct. 28, 1996 and entitled "Asymmetric Multiple Electrode Support Structures," which is incorporated herein by reference.

Each spline element 152 carries an array of multiple transmitting electrodes TE and at least one return electrode RE, as previously described. Each spline element 152 thus comprises a locating probe. The structure 150 comprises an ordered array of multiple location probes, which, in use, create a waveform field 162 about the space bounded by the spline elements 152.

FIG. 6 shows an operative element 172 movable within the energy waveform field 162. The operative element 172 carries a sensing element 174.

As before described, a central processing unit 164 sequentially connects the waveform output of an oscillator 166 through a switch unit 168 to the transmitting electrodes TE on each spline element 152 (for example, beginning with the most proximal and moving distally), while coupling the respective most distal return electrode RE of the spline element 152 to isolated ground or patient ground 170. The central processing unit 164 also sequentially couples the electrodes TE and the sensing electrode 174 on the operative element 172 through a switch unit 169 and a DAQ 171 to acquire a differential voltage along a grid of intersecting iso-potential surfaces TP in the energy waveform field 162, in the same manner shown for the probes 106 and 108 in FIGS. 4 and 5. The differential comparison derives either an in-phase relationship or an out-of-phase relationship between $W_S$ and $W_O$, depending upon the location of the sensing element 174 relative to the transmitting electrodes along each elongated spline element 152.

The central processing unit 164 can also perform a differential comparison between the signal amplitude of the sensed waveform $A_S$ and the signal amplitude of the waveform at the switched-on electrode $A_O$ where the phase transition occurs, to derive the latitudinal orientation of the sensing element 174 perpendicular to each spline element 152.

II. Differential Voltage Analysis
A. Relative Proximity Derivation

Figure 8:
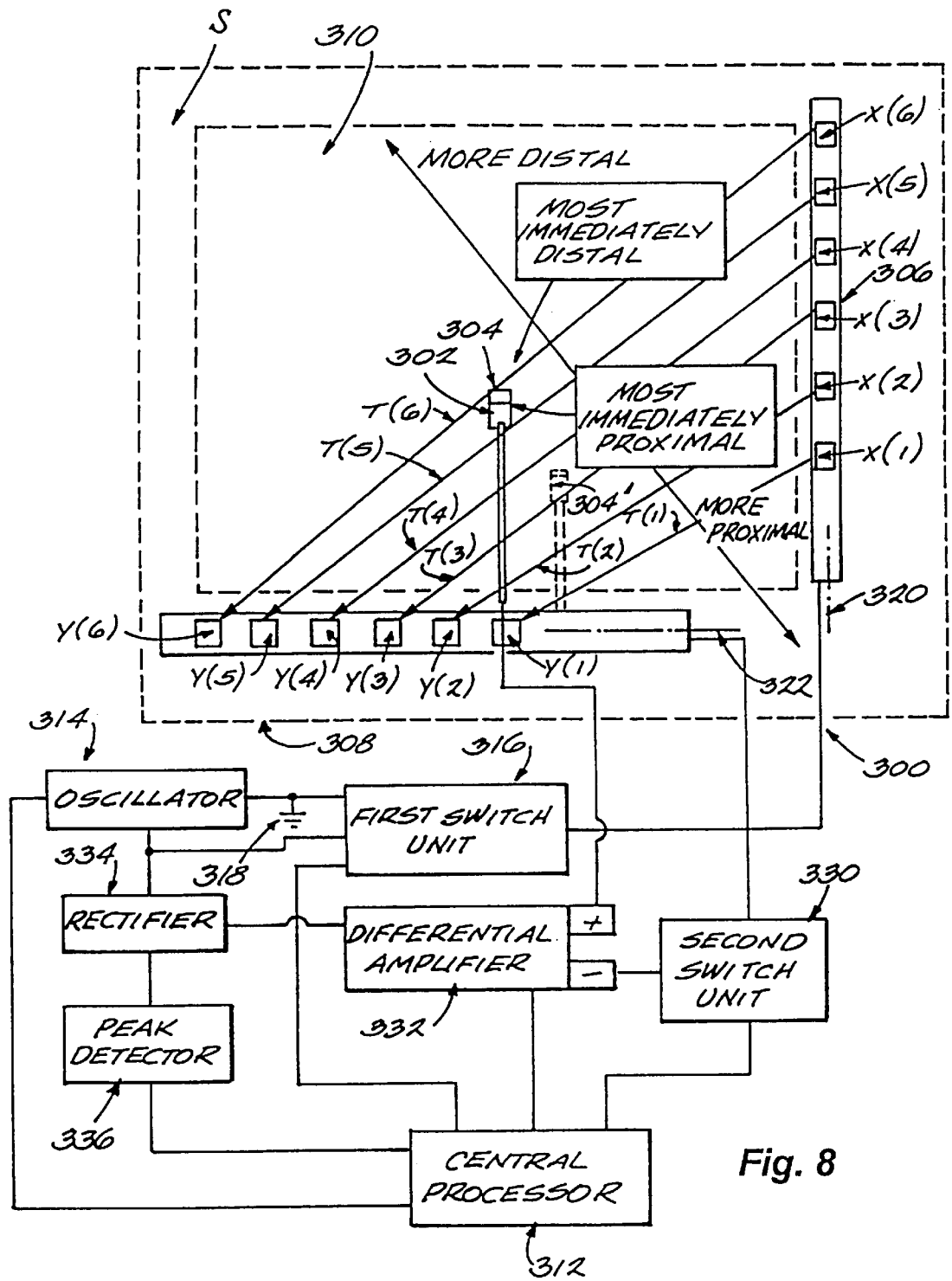
FIG. 8 is a diagrammatic plan view of a system to locate the position of an operative element within a space using voltage differential comparisons between two locating probes.

FIG. 8 shows an alternative embodiment of system 300 that locates an operative element 302 within a space (designated S), using differential voltage analysis instead of differential waveform analysis. The system generates an energy waveform field 310 between two locating probes 306 and 308. Each locating probe 306 and 308 includes at least one transmitting electrode, which are designated X(1) to X(6) for probe 106 and Y(1) to Y(6) for probe 108. The operative element 302 carries a sensing element 304.

In the illustrated embodiment, the locating probes 306 and 308 are positioned so that their elongated axes, respectively 320 and 322, are not parallel, but extend at some angle. In the illustrated embodiment, the angle is about 90°, but other smaller or larger angles can be used. Alternatively, because differential voltage analysis is employed, the locating probes 306 and 308 in this embodiment can be located in a parallel, mutually facing relationship.

The operation of the system 300 is governed by a central processing unit 312. The central processing unit 312 connects the waveform output of an oscillator 314 through a first switch unit 316 to transmit the waveform from all transmitting electrodes on one probe 306 to all the electrodes on the other probe 308, which are coupled to the isolated patient ground 318. For this reason, the probe 306 will be called the "transmitting probe" and the probe 308 will be called the "receiving probe." The receiving and transmitting functions of the probes 306 and 398 can be reversed. The generated waveform field 310 extends between the transmitting probe 306 and the receiving probe 308. The waveform can be generated simultaneously between all electrodes or sequentially along the axis of the probes 306 and 308.

As FIG. 8 shows, the waveform field 310 includes iso-potential surfaces T(1) to T(6), which extend between the transmitting-receiving electrode pairs X(1)–Y(1) to X(6)–Y(6).

The central processing unit 312 conditions a second switch element 330 to couple each switched-on electrode on the transmitting probe 306 in succession to inverting (−) input of a differential amplifier 332, while coupling the sensing element 304 to the noninverting (+) input. The amplifier subtracts the electrical potential measured by the electrode coupled to the inverting input from the electrical potential measured by the sensing element 304. The differential potential times the gain of the amplifier 332 constitutes the input to a rectifier 334.

A detector 336 senses the peak voltage, and the rectifier 334 senses the synchronization of the phase of the voltage signal relative to the phase of the oscillator 314. The central processing unit 312 registers the peak voltage and the synchronization in association.

The synchronization of the phase of the output voltage signal of the amplifier 332 relative to the phase of the oscillator 314 will vary depending upon the location of the most immediately distal iso-potential surface to the sensing electrode 304.

More particularly, the output voltage signal of the amplifier 332 will be in-phase with respect to the phase of the oscillator 314 only when the differential amplitude is measured along the iso-potential surface which is most immediately distal to the sensing electrode 304. In FIG. 8, the most immediate distal iso-potential surface to the sensing electrode 304 is T(6), which lies between electrode pairs X(6)–Y(6). The output voltage signal of the amplifier 332 will be out-of-phase with respect to the phase of the oscillator 314 for the differential amplitudes measured along the most immediately proximal iso-potential surface to the sensing electrode 304, and along all other more proximal iso-potential surfaces. In FIG. 8, the most immediate proximal iso-potential surface is T(5), which lies between electrode pairs X(5)–Y(5) and the remaining more proximal surfaces T(4) to T(1) lie between electrode pairs X(4)–Y(4) to X(1)–Y(1).

By way of another example, assuming another position of the sensing element 304' (shown in phantom lines in FIG. 8), the output voltage signal of the amplifier 332 will be in-phase with respect to the phase of the oscillator 314 only when the differential amplitude is measured along the iso-potential surface T(4), which is the most immediately distal to the sensing electrode 304'. The output voltage signal of the amplifier 332 will be out-of-phase with respect to the phase of the oscillator 314 for the differential amplitudes measured along the most immediate proximal iso-potential surface T(3) and all other more proximal iso-potential surfaces T(2) and T(1).

Differential voltage analysis can also be used in association with the composite probe structure 150 shown in FIG. 6 or any of the structures shown earlier.

III. Three-Dimensional Navigation Systems

A. Establishing a Three-Dimensional Navigation System (Using a Waveform Differential Analysis)

Figure 9:
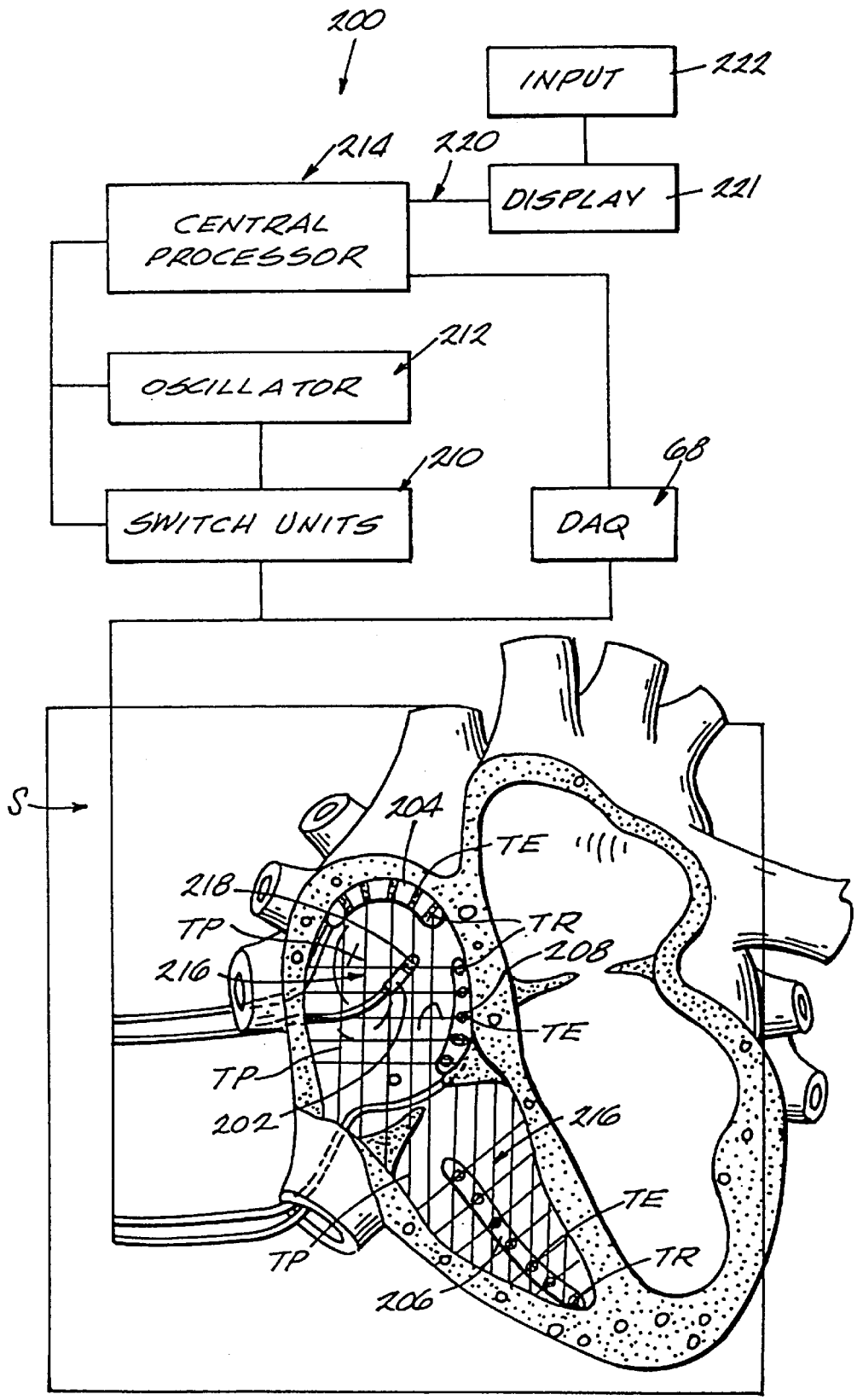
FIG. 9 is a diagrammatic view of a three-dimensional system for locating the position and guiding movement of an operative element within a heart.

FIG. 9 shows a representative implementation of a three-dimensional navigation system 200, which includes three locating probes 204, 206, and 208 positioned within a space S. In the illustrated embodiment, the space S comprises the interior of a heart. In use, the system 200 locates and guides an operative element 202 within the heart. The operative element 202 can serve to sense electrical activity in the heart to locate potential ablation sites, or to transmit energy to pace heart tissue, measure impedance, or to ablate. Alternatively, the operative element 202 can include an imaging element to image tissue, anatomic structures, or lesions formed within the heart. Also, the operative element can include a cannula to penetrate heart tissue for the purpose of injecting an ablation media, or to inject a drug or gene therapy agent.

For purpose of illustration, the three locating probes 204, 206, and 208 are purposely situated within the heart to provide spaced-apart navigational points for locating the operative element 202. Furthermore, the probes 204, 206, and 208 are located at different coordinate planes, to create a three-dimensional navigational grid and make triangulation possible.

In the illustrated embodiment, the probes 204, 206, and 208 are individually placed at or near known anatomic regions of the heart using, for example, fluoroscopy or another imaging technology, such as ultrasound. This is because potential ablation sites within the atria are typically identified by reference to an anatomic landmark within the heart.

It should be appreciated that a single locating probe or multiple locating probes may be positioned essentially in any region within the heart or in any tissue or vascular region surrounding the heart for purposes of establishing navigational points of reference to locate the operative element 202. Any region of placement with the body that can be imaged by fluoroscopic or other imaging technology can be selected as a potential navigational site. The region of placement therefore does not have to represent a particular fixed anatomic site. For example, establishing a three-dimensional navigation system for use within a given heart chamber, one or more locating probes can be located within the heart chamber, another one or more probes may be located in a different chamber, and yet another one or more locating probes can be located at an epicardial location outside the interior of the heart.

In the illustrated embodiment, the first locating probe 204 is positioned in region of the high right atrium; the second locating probe 206 is positioned in the region of the right ventricular apex; and the third locating probe 208 is positioned in the region of the coronary sinus. The three probes 204, 206, and 208 are located on different coordinate planes, so that the probe axes extend in mutually nonparallel relationships.

Each locating probe 204, 206, and 208 includes multiple transmitting electrodes TE and a distal return electrode TR, which function in the manner previously described and shown in FIG. 1. A transmitting electrode TE and the return electrode TR on each probe 204, 206, and 208 are coupled via electronic switch units 210 to an oscillator 212 to create an energy waveform field 216.

The operative element 202 carries a sensing element 218, which can also can serve as an ablation electrode or as sensing electrode. The sensing element 218 is coupled to the central processing unit 214 in the manner previously described to sense the waveform quantity $W_S$ within the field 216.

A DAQ 68 acquires differential waveforms along multiple iso-potential surfaces TP, one associated with each electrode TE on each probe 204, 206, and 208. As shown in FIG. 9, because the probes 204, 206, and 208 are located at different coordinate planes, the multiple iso-potential surfaces TP form intersection points within the field 216.

The central processing unit 214 employs the DAQ 68 previously described (see FIG. 3) to differentially compare $W_S$ to $W_0$ for each switched-on electrode TE and locate regions of phase transitions relative to each probe 204, 206, and 208. In addition, the central processing unit 214 can also perform a differential comparison between the signal amplitude of the sensed waveform $A_S$ and the signal amplitude of the waveform at the switched-on transmitting electrode $A_0$ where the phase transition occurs to derive the latitudinal orientation of the sensing element 218 perpendicular to the axis of each probe 204, 206, 208.

The central processing unit 214 generates a position-indicating output 220, which locates the sensing element 218 (and thus the operative element 202 itself) within the matrix of intersecting iso-potential surfaces TP generated by the three probes 204, 206, and 208.

B. Establishing a Three-Dimensional Navigation System (Using an Iterative Voltage Analysis)

Figure 17:
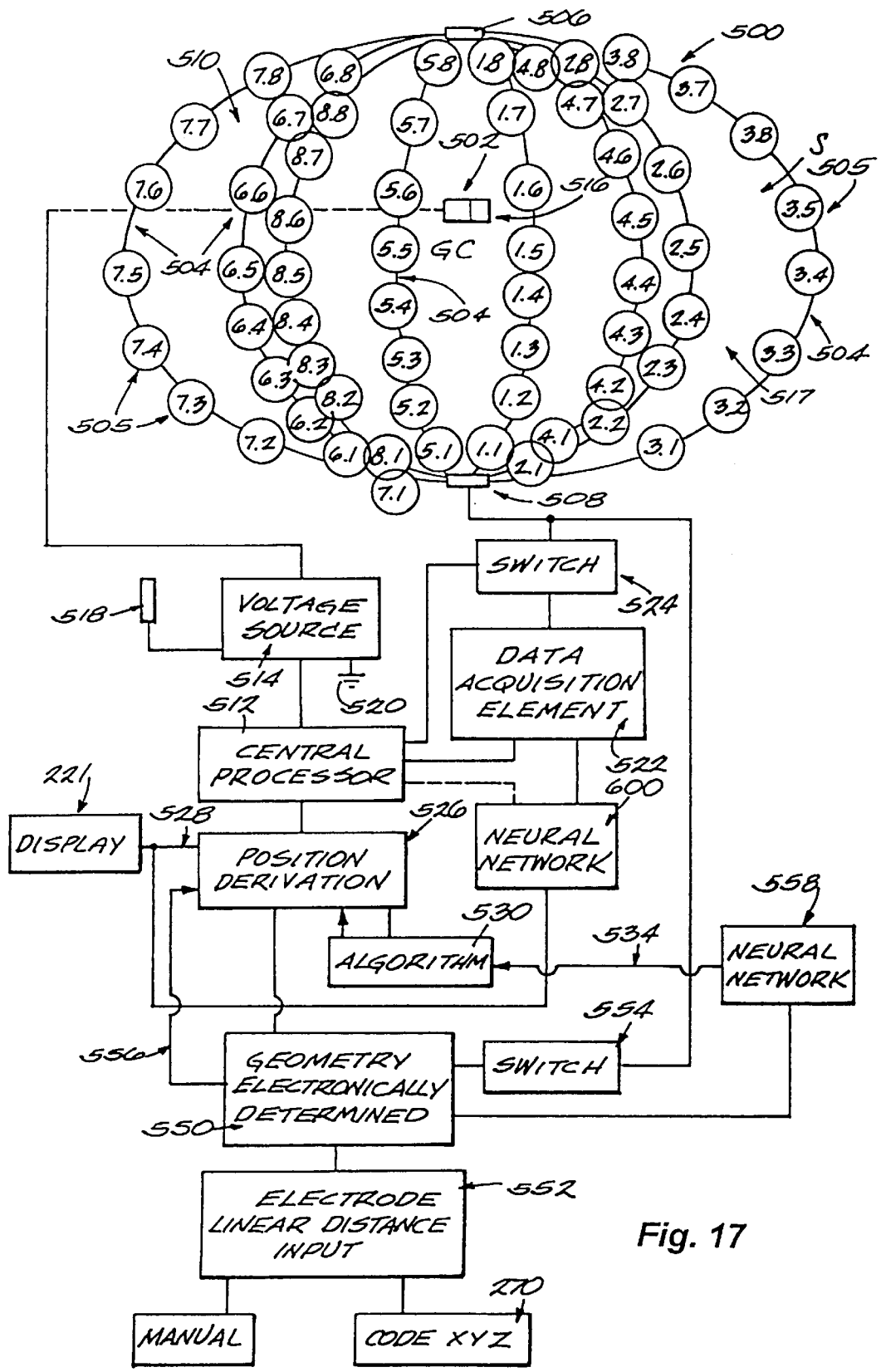
FIG. 17 is a perspective and somewhat diagrammatic view of a composite three-dimensional basket structure of multiple locating probes usable in association with a central processing unit to derive a location-indicating output using an iterative voltage distribution analysis.

FIG. 17 shows a three dimensional system 500, which conducts an iterative differential voltage analysis to determine the location of an operative element 502 within a space S peripherally bounded by multiple locating probes 504. In FIG. 17, the multiple locating probes 504 are assembled together by a distal hub 506 and a proximal base 508 into a composite, three-dimensional basket structure 510 of the type previously shown and described in FIG. 6. However, it should be appreciated that the multiple locating probes 504 need not be assembled together in a composite structure, but exist as separate probes located about the space S, in the manner shown in FIG. 9, as previously described.

The composite structure 510, however, is well suited for use within the heart and can perform other functions in addition to navigation. For example, the composite structure 510 can serve to transmit electrical signals to pace heart tissue or to characterize the electrical characteristics of the tissue by acquiring tissue impedance measurements. The composite structure can also serve to sense electrical activity in myocardial tissue to acquire electrograms for heart mapping procedures.

The composite structure 510 shown in FIG. 17 includes eight locating probes 504, and each probe, in turn, carries eight electrodes 505, for a total of sixty-four electrodes 505 positioned about the space S. FIG. 17 identifies the electrodes 505 by the designation (A,B), where A=1 to p and B=1 to e, where p is the total number of probes 504 and e is the number of electrodes 505 on each probe 504 (in the illustrated embodiment, p=8 and e=8).

The system 500 includes a central processing unit 512, which couples a voltage source 514 to a transmitting electrode 516 carried by the operative element 502. In FIG. 17, an indifferent electrode 518, carried as a patch on the exterior of the patient, comprises the voltage return, which is, in turn, coupled to isolated or patient ground 520. Alternatively, another electrode carried by the operative element 502 can serve as the voltage return. The electrode 516 creates a voltage field 517 within the space S, which varies in detected amplitude at each probe electrode 505 according to its distance from the transmitting electrode 516.

The system 500 includes a data acquisition element 522 coupled to the central processing unit 512 and to a switch element 524. The switch element 524 individually conditions each electrode (A,B) to sense voltage existing at its location within the field 517, which the data acquisition element 522 samples and holds, in the manner previously described, e.g., see FIG. 3.

Figure 18:
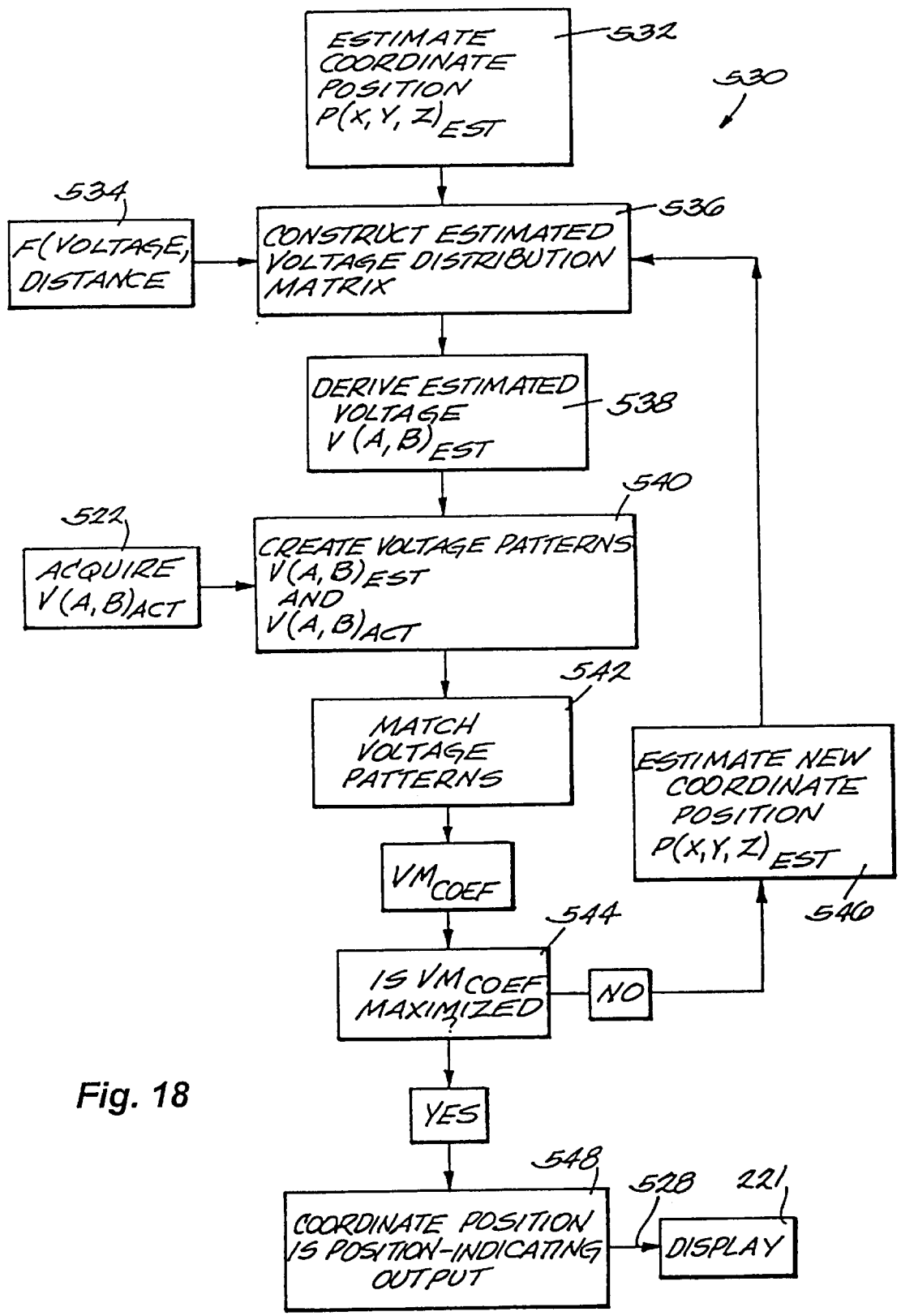
FIG. 18 is a flow chart showing the steps of an algorithm that the central processing unit shown in FIG. 17 can use to derive a location-indicating output using an iterative voltage distribution analysis.

The central processing unit 512 includes a processing component 526 which derives a position-indicating output 528 based upon the voltage distribution sensed by the electrodes (A,B) on the probes 504. FIG. 18 shows the steps of a preferred algorithm 530 for deriving the output 528.

As FIG. 18 shows, the algorithm 530 includes, as a first step 532, establishing an estimated coordinate position $P(x, y, z)_{EST}$ for the transmitting electrode 516 on the operative element 502 within the space S, where x is the x-field coordinate, y is the y-field coordinate, and z is the z-field coordinate. For example, $P(x, y, z)_{EST}$ can be initially arbitrarily set at P(0,0,0), which is at the geometric center of the voltage field 517 (designated as GC in FIG. 17). Alternatively, differential waveform analysis, or differential voltage analysis, or amplitude analysis, as described above, alone or in combination, can also be used to more accurately estimate $P(x, y, z)_{EST}$. By way of another example, position indicating methodologies disclosed in copending patent application Ser. No. 08/320,301, filed Oct. 11, 1994 and entitled "Systems and Methods for Guiding Movable Electrode Elements Within Multiple Electrode Structures" can also be used to provide a more accurate initial position estimate $P(x, y, z)_{EST}$. To increase processing efficiencies, multiple signals that are orthogonal from a signal processing standpoint (for example, waveform signals of different frequencies, waveform signals of the same frequency but which differ by 90° in phase, and waveforms from uncorrelated white noise sources) may be transmitted simultaneously in the manner shown in FIG. 22 (as will be described in greater detail later).

In the next step 536, the algorithm 530 computes the distance $\Delta D(A,B)$ between each probe electrode (A,B) and the transmitting electrode 516 at $P(x,y,z)_{EST}$. The distances $\Delta D(A,B)$ can be normalized to facilitate analysis. The algorithm then applies a preestablished, mathematical voltage-to-distance function 534 to derive the estimated voltage $V(A,B)_{EST}$ at each electrode (A,B), based upon $\Delta D(A,B)$. In effect, the algorithm 530 constructs an estimated voltage distribution matrix, which would exist, according to the function 534, if $P(x, y, z)_{EST}$ was the actual voltage transmission point. The voltage-to-distance function 534 can be empirically determined or be based upon finite element analysis and stored in memory accessible to the central processing unit 512. As a next step 538, the algorithm 530 derives an estimated or expected voltage differential $V(A, B)_{EST}$ for each electrode 505.

Figure 19:
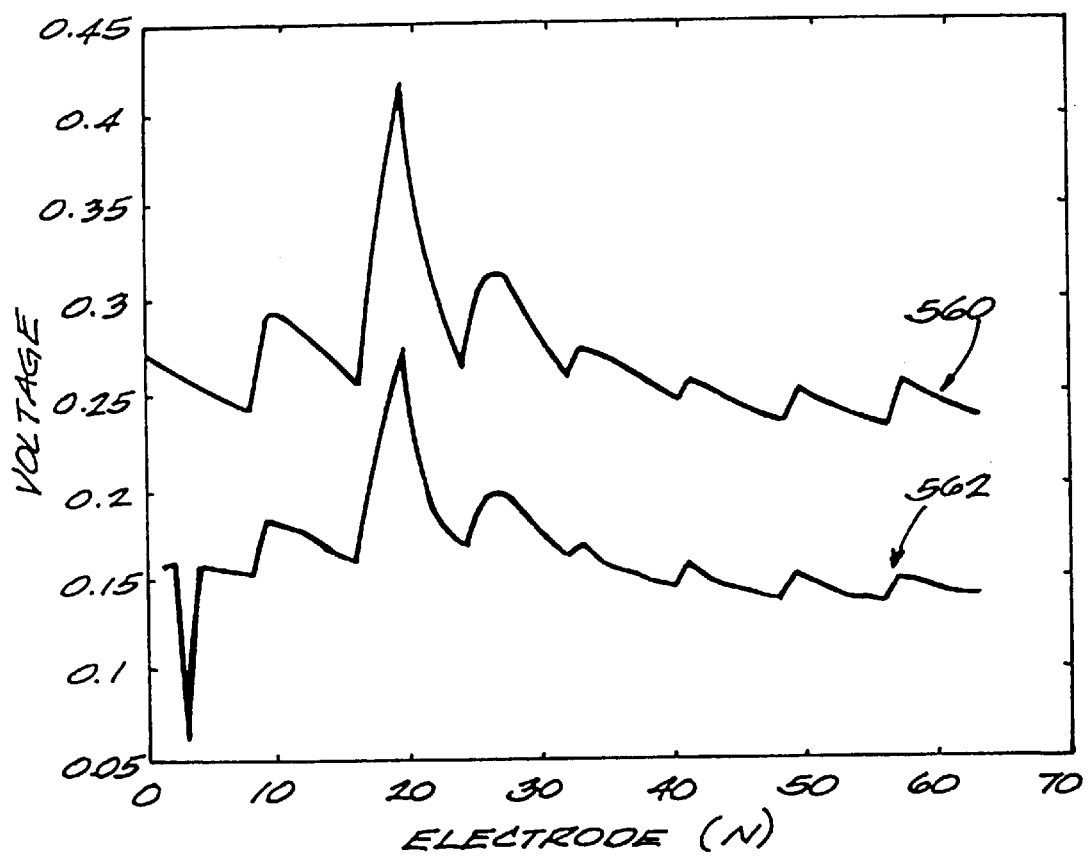
FIG. 19 shows voltage distribution patterns, one actual and the other estimated, which the algorithm shown in FIG. 18 iteratively matches in deriving a location-indicating output.

In the next step 540, the algorithm 530 receives as input $V(A, B)_{ACT}$, where $V(A, B)_{ACT}$ is the measured voltage value acquired by operation of the data acquisition element 522 at each probe electrode (A,B). As FIG. 19 shows, the algorithm 530, in this step 540, creates a measured voltage distribution pattern 560 based upon the values for $V(A, B)_{ACT}$, which plots (on the Y-axis) the sensed voltage values for each electrode (numbered 1 to 64 on the X-axis). The algorithm 530 creates an estimated voltage distribution pattern 562 based upon the values for $V(A, B)_{EST}$, which plots (on the Y-axis) the estimated voltage values for each electrode (again numbered 1 to 64 on the X-axis).

As a next step 542, The algorithm 530 matches the voltage distribution pattern 560 with the voltage distribution pattern 562 to derive a voltage matching coefficient $VM_{COEF}$.

The value of the voltage matching coefficient $VM_{COEF}$ for a given $P(x, y, z)_{EST}$ increases as $P(x, y, z)_{EST}$ coincides with the actual location of the transmitting electrode 516. That is, the value of the voltage matching coefficient increases in relation to the proximity of the transmitting electrode 516 to the estimated position $P(x, y, z)_{EST}$.

The central processing unit 512 can derive the matching coefficient $VM_{COEF}$ in various conventional ways, for example, by employing pattern matching; matched filtering; or cross correlation. Examples of using these techniques to derive matching coefficients appear in copending U.S. patent application Ser. No. 08/390,383, filed Feb. 17, 1995 and entitled "Systems and Methods for Examining Heart Tissue Employing Multiple Electrode Structures and Riving Electrodes," which is incorporated herein by reference.

In the next step 544, the algorithm 530 determines whether $VM_{COEF}$ is the "best", i.e., whether it is maximized under the processing rules applied. For the first iteration, and for all subsequent iterations were $VM_{COEF}$ is not maximized, the algorithm 530 applies (in step 546) a preselected incremental correction factor Δx to the x coordinate, factor Δy to the y coordinate, and factor Δz to the z coordinate of the estimated position of the transmitting electrode 516 to create a new estimated position P(x+Δx, y+Δy, z+Δz)), which become the new coordinates for an estimated position $P(z, y, z)_{EST}$. The algorithm 530 then loops through the foregoing steps 536, 538, 540, 542, and 544, to derive an iterated voltage matching coefficient $VM_{COEF}$ based upon the new estimated location. The algorithm 530 iteratively selects Δx, Δy, and Δz until a best (maximum value) voltage matching coefficient $VM_{COEF}$ is achieved in step 544. The coordinates $P(x,y,z)_{EST}$ at the best, maximum voltage matching coefficient $VM_{COEF}$ become the position-indicating output 528, as shown in step 548 in FIG. 18.

There are various ways in which the iteration of the x-, y-, and z- coordinates can be accomplished. For example, the algorithm 530 can iterate the x-coordinate alone (keeping the y- and z-coordinates constant) until a best voltage matching coefficient $VM_{COEF}$ is achieved, then fix the x-coordinate at that value and iterate the y-coordinate alone (while also keeping the z-coordinate constant) until another best voltage matching coefficient $VM_{COEF}$ is achieved, and then fix the y-coordinate at that value and iterate the z-coordinate alone (keeping the previously fixed x- and y-coordinates constant), until another best voltage matching coefficient $VM_{COEF}$ is achieved. The algorithm 530 then loops back through this process, until the best voltage matching coefficient $VM_{COEF}$ is obtained for each local x-, y-, and z-coordinate, as well as for $P(x, y, z)_{EST}$ overall.

Alternatively, the x-, y-, and z-coordinates can be simultaneously incremented to maximize the voltage matching coefficient $VM_{COEF}$ for $P(x, y, z)_{EST}$, using, for example, a conventional maximum gradient method.

Due to its iterative nature, the algorithm 530 shown in FIG. 18 corrects for distortion of the locating probes caused by exposure to dynamic conditions within a body cavity, such as within a beating heart chamber. The iterative nature of the algorithm 530 also corrects for electrical "noise" caused, for example, by the inherent electrical resistance of the electrodes and associated electrical wiring.

Furthermore, the iterative differential voltage analysis just described also makes possible the generation of an error signal, should the position of the operative element 502 stray beyond the energy field 517. Should this event occur, the estimated voltage and the actual voltage become mirror images. This outcome, when sensed by the central processing unit 512, can command the generation of an out-of-field error signal.

In an alternative embodiment, the central processing unit 512 can incorporate a neural network 600 (see FIG. 17), which has been trained on experimentally acquired sets of voltage distribution data correlated with known positions of the transmitting electrode 516. Once the training phase is completed, the network 600 can instantaneously output the position-indicating output 528, based upon input from the data acquisition element 522 of voltage distribution data sensed by the probe electrodes 505 during transmission of voltage by the electrode 516.

C. Displaying Three-Dimensional Navigational Information

As FIG. 9 shows, the position-indicating output 220 (or, in the embodiment shown in FIG. 17, the output 528) is preferably processed for viewing on a display device 221. In a preferred embodiment (see FIG. 10), the central processing unit 214 includes an input 222 that receives information pertaining to the position and orientation of the locating probes 204, 206, and 208 within the heart. The input 222 also receives information pertaining to the shape and size of each locating probe 204, 206, and 208. The central processing unit 214 includes functional algorithms 224, which set guidance parameters based upon the input information. These guidance parameters are used by the central processing unit 214 to analyze the spatial variations of the electric waveform field generated by the locating probes 204, 206, and 208. The guidance parameters govern the processing of differential comparison data to create the position-indicating output 220 for display on the device 221. The processed position-identifying output aids the physician in locating and guiding the operative element 202 in real time.

In a preferred embodiment (see FIG. 10), the probes 204, 206, and 208 of the system 200 are members of a family 209 of locating probes. The various probes comprising the family 209 are characterized by different geometries, different densities of transmitting and return electrodes, and other structural and functional differences. In this embodiment, each probe 204, 206, and 208 within the family 209 includes an identification component 270. The identification component 270 carries an assigned identification code XYZ. The code XYZ identifies the shape and size of the electrode-supporting part of the probe and the distribution of electrodes carried thereon, in terms of the number of electrodes and their spatial arrangement. The structure-specific information contained in the code XYZ aids the central processing unit 214 in creating a positioning matrix based upon the locating probes when deployed.

In the illustrated embodiment (see FIG. 10), the coded component 270 is located within the handle 230 attached to the proximal end of the catheter tube 232 that carries the locating probe 204, 206, and 208. However, the component 270 could be located elsewhere in relation to the locating probe.

The coded component 270 is electrically coupled to an external interpreter 278 when the probe is coupled to the central processing unit 214 for use. The interpreter 278 inputs the code XYZ that the coded component 270 contains. The interpreter 278 electronically compares the input code XYZ to, for example, a preestablished master table 280 of codes contained in memory. The master table 280 lists, for each code XYZ, the structure-specific information required to create the positioning matrix to locate and guide the operative element 202 within the waveform field 216. The functional algorithms 224 of the central processing unit 214 set location and guidance parameters based upon the code XYZ.

Because knowledge of the physical characteristic of the locating probe and the spatial relationship of the electrodes it carries is important in setting accurate location and guidance parameters, the algorithms 224 preferably disable the central processing unit 214 in the absence of a recognizable code XYZ. Thus, only probes of the family 209 possessing a coded component 270 carrying the appropriate identification code XYZ can be used in association with the processing element 214.

Figure 11:
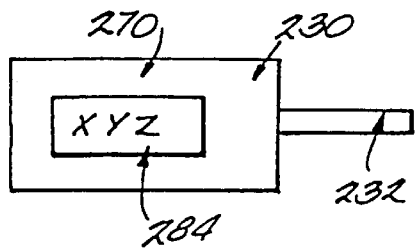
FIGS. 11 and 12 are plan views, somewhat diagrammatic in form, showing alternative implementations of a code to identify the geometry of a locating probe, which code serves as one of the inputs shown in FIG. 10.

The coded component 270 can be variously constructed. It can, for example, take the form of an integrated circuit 284 (see FIG. 11), which expresses in digital form the code XYZ for input in ROM chips, EPROM chips, RAM chips, resistors, capacitors, programmed logic devices (PLD's), or diodes. Examples of catheter identification techniques of this type are shown in Jackson et al. U.S. Pat. No. 5,383,874, which is incorporated herein by reference.

Figure 12:
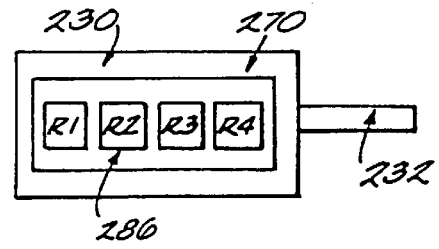

Alternatively, the coded component 270 can comprise separate electrical elements 286 (see FIG. 12), each one of which expresses an individual characteristic. For example, the electrical elements 286 can comprise resistors (R1 to R4), comprising different resistance values, coupled in parallel. The interpreter 278 measures the resistance value of each resistor R1 to R4. The resistance value of the first resistor R1 expresses in preestablished code, for example, the number of electrodes on the probe. The resistance value of the second resistor R2 expresses in preestablished code, for example, the distribution of electrodes on the probe. The resistance value of the third resistor R3 expresses in preestablished code, for example, the size of the probe. The resistance value of the fourth resistor R4 expresses in preestablished code, for example, the shape of the probe.

It should be appreciated that the three-dimensional basket structure 510 shown in FIG. 17 can also carry an identification component 270 having an assigned identification code XYZ to identify the shape and size of the multiple probe structure 510 and the distribution of electrodes carried thereon. In this arrangement, the structure-specific information contained in the code XYZ aids the position derivation component 528 and algorithm 530 in FIG. 18 to construct the estimated voltage distribution matrix and analyze sensed voltage differentials.

The central processing unit 512 can also include a component 550 (see FIG. 17), which electronically determines structure-specific information to construct the estimated voltage distribution matrix and analyze sensed voltage differentials. In this arrangement, the component 550 commands, in sequence, the transmission of voltage from the source 514 through a switch unit 554 from each probe electrode (A,B) to the indifferent electrode 518, while sensing voltage with the remaining probe electrodes through the switch 524 and data acquisition element 522. The component 550 thereby acquires a first set of data from which the voltage differential between every electrode (A,B) can be obtained.

Figure 10:
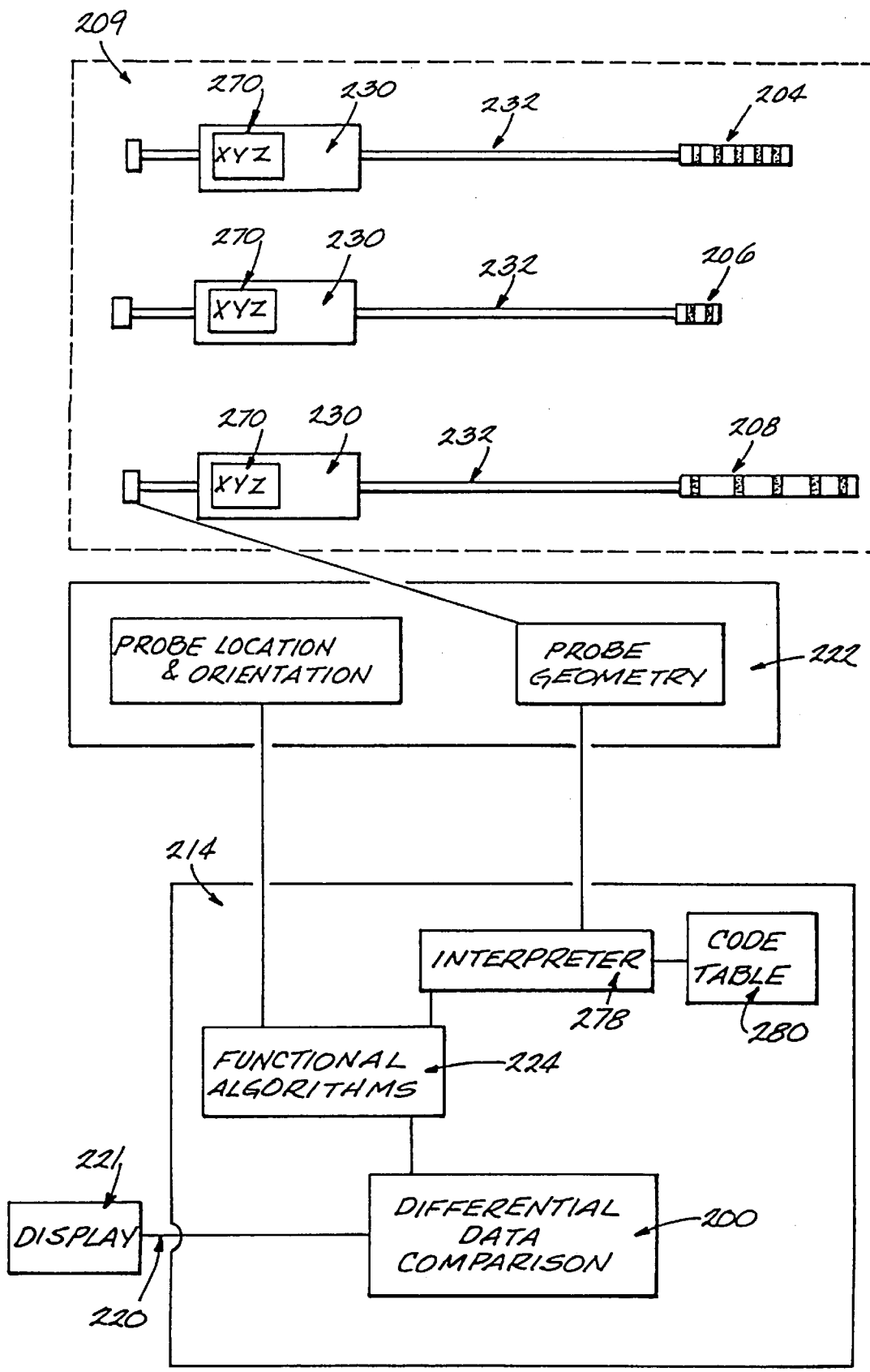
FIG. 10 is a diagrammatic view of a portion of the system shown in FIG. 9, showing the inputs which set the system parameters to guide the creation of a position-identifying output.

The component 550 includes an input 552, through which the component 550 acquires data relating to the linear distance between adjacent electrodes on each probe 504. Typically, the electrodes 505 on each probe 504 will be spaced apart by manufacturer at the same linear distance, so that will typically be only a single linear distance to input. The physician can manually enter the linear distance information through the input 522. Alternatively, the input 552 of linear distance information can be carried by a coded component 270 as earlier described as shown in FIG. 10, which is inputted automatically upon coupling the probe structure 510 to the central processing unit 512. In this arrangement, more complex linear distance information can be readily inputted. The linear distance information comprises a second set of data.

Knowing the linear distance information between adjacent electrode 505 contained in the second set of data, and the sensed voltage differentials between these electrodes 505 contained in the second set of data, the component 520 then derives using conventional estimating techniques the distances between other, nonadjacent electrodes 505, both along a probe 504 and between probes 504. The component 550 generates a geometric output 556, which, like the code XYZ, the output 556 identifies the shape and size of the multiple probe structure 510 and the distribution of electrodes 505 carried thereon.

The output 556 also provides the basis for calculating the interior volume of the structure 510. In the heart, the interior volume of the structure 510 typically will conform to the interior volume of the heart chamber it occupies. The interior volume will also typically dynamically adjust to the changing heart chamber volumes during systole and diastole. The component 550 therefore makes possible the electrical analysis, for therapeutic or diagnostic purposes, of heart chamber volumes and the changes in heart chamber volume during systole and diastole. The component 550 can thereby be used, independent of or in association with a navigation function, to characterize heart morphology and function.

In another embodiment, the component 550 can incorporate a neural network 558 (see FIG. 17) to generate in situ the distance-to-voltage function 534 particular to a given structure 510, based upon the electrically sensed geometry and distribution of electrodes on the structure 510. The neural network 558 is first trained on a known set of data that have been previously acquired experimentally. For example, using a back-propagation model, the network 558 can be trained to predict a voltage-to-distance function 534 based upon structure-specific information. Once the training phase is completed, the network 558 can be used to predict the voltage-to-distance function in situ.

Figure 13:
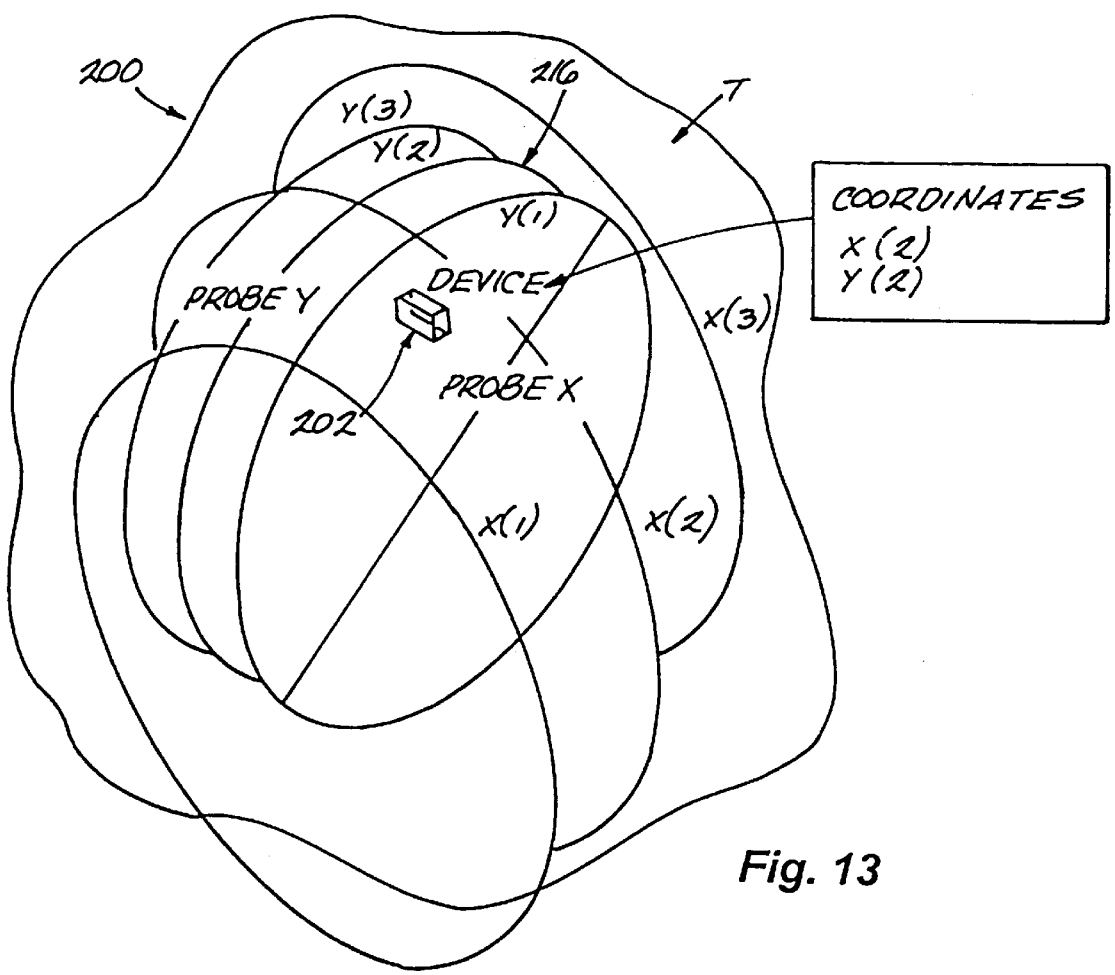
FIG. 13 is a representative virtual image that the system shown in FIG. 10 generates from the position-identifying output.

Based upon information received by the input 222, the central processing unit 214 (or 512 in FIG. 17) electronically constructs a three-dimensional coordinate system representing a virtual image 290 of the energy field 216 (or 217 in FIG. 17) and surrounding tissue mass T. FIG. 13 shows a representative virtual image 290 based upon two locating probes. In FIG. 13, the virtual image 290 indicates the position of the locating probes (designated "Probe X" and "Probe Y" in FIG. 13), as well shows the geometry and location of the iso-potential surfaces (designated "X(1) to X(3)" and "Y(1) to Y(3)" in FIG. 13). The virtual image 290 shows the position of the operative element 202 (designated "Device" in FIG. 10) within the energy field 216, as well as displays the coordinates of the operative element (designated "Coordinates: X(2) Y(2)" in FIG. 10). The central processing unit 214 continuously performs the differential comparisons and updates the virtual image 290 to provide a real time display for viewing by the physician.

IV. Using Multiple Waveforms

The locating and navigation systems of the type previously described create an energy field by applying a single waveform. Multiple waveforms can be simultaneously applied to gain processing efficiencies, provided the different waveforms are orthogonal from a signal processing standpoint. Examples of different, orthogonal processing signals includes waveform signals of different frequencies, waveform signals of the same frequency but which differ by 90° in phase, and waveforms from uncorrelated white noise sources.

A. Differential Waveform Analysis Using Different Waveforms

Figure 20:
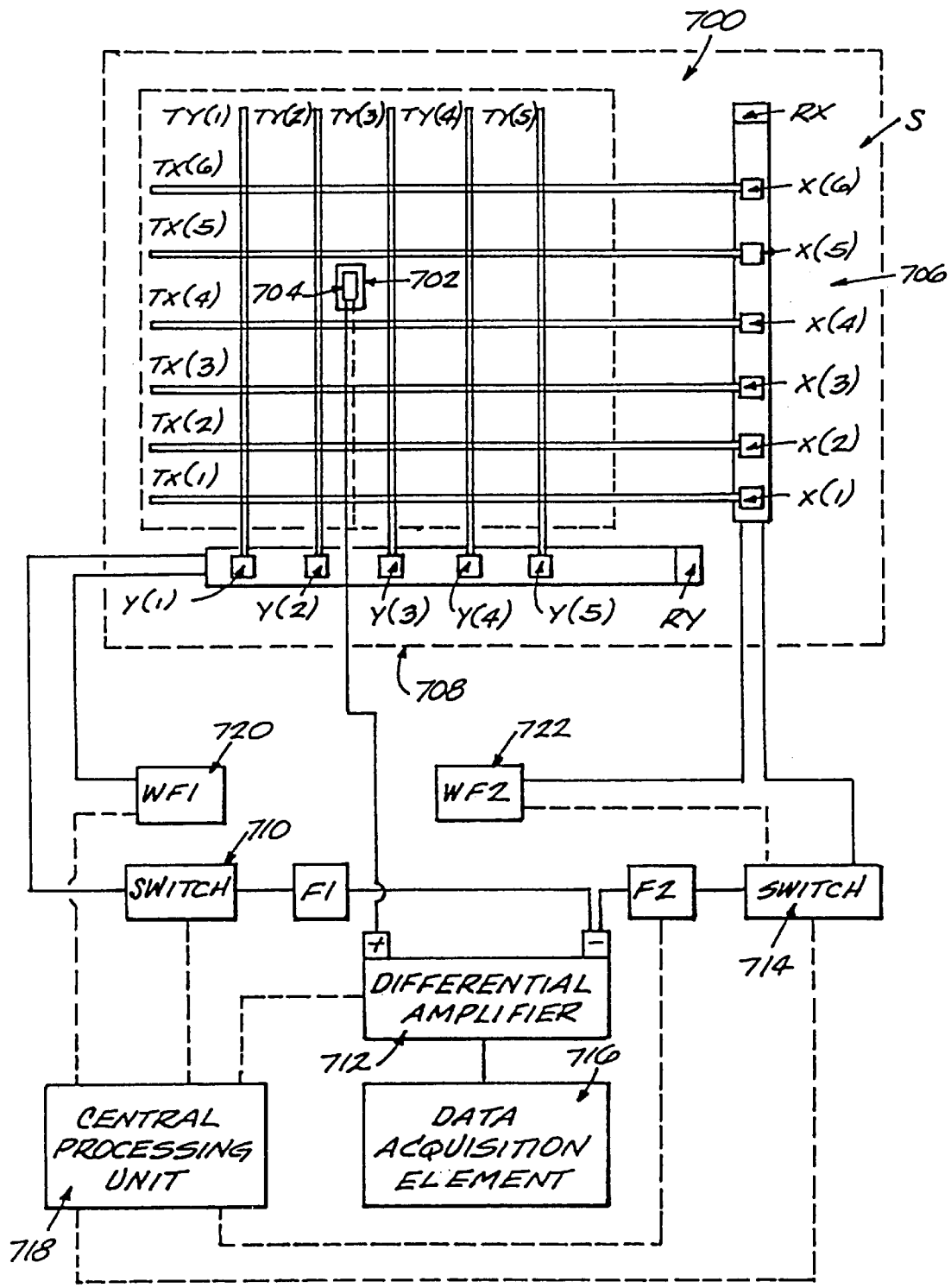
FIG. 20 is a diagrammatic plan view of a system to locate the position of an operative element within a space by generating multiple frequency waveforms from multiple locating probes.

FIG. 20 shows a system 700 that locates an operative element 702 within a space S by generating different waveforms using two probes 706 and 708.

In many respects, the system 700 shares common elements with the system 100 shown in FIG. 4. The locating probe 706 and 708 are generally like the locating probes 106 and 108 shown in FIG. 4. The electrodes carried by the locating probe 706 are designated X(1) to X(6) and the electrodes carried by the locating probe 708 are designated Y(1) to Y(5). Each locating probe 706 and 708 also includes a return electrode, designated RX for probe 706 and RY for probe 708. As in FIG. 4, the locating probes 706 and 708 are positioned relative to each other in a non-parallel relationship. As in the FIG. 4, the operating element 702 carries a sensing element 704.

The system 700 includes a first waveform source WF1, which is coupled to the probe 708. The system also includes a second waveform source WF2. The first waveform WF1 is different than but orthogonal to the second waveform WF2. In the illustrated embodiment, the waveforms WF1 and WF2 have different frequencies, and the sources comprise separate oscillators 720 and 722.

The probe 708 is coupled via a switching unit 710 and a first filter F1 for the waveform WF1 to the inverting (−) input of a differential amplifier 712. The probe 706 is also coupled by a second switching unit 714 and a second filter F2 for the WF2 is also coupled to the inverting (−) input of the differential amplifier 712. The sensing element 704 carried by the operative element 702 is coupled to the noninverting (+) input of the differential amplifier 712. The output of the differential amplifier 712 is coupled to a data acquisition element 716. The data acquisition element 716 includes a rectifier, peak detector, sample and hold element, and analog-to-digital converter coupled as shown in FIG. 3 to process the differential output in the manner previously described, under the control of a central processing unit 718.

Under the control of the central processing unit 718, the multiple oscillators 720 to 722 simultaneous apply the waveform WF1 to the electrode Y(1), for return through the return electrode RY, and the different waveform WF2 to the electrode X(1), for return through the return electrode RX.

The central processing unit 718 operates the switch units 710 and 714 to simultaneously acquire two differential voltages, one for waveform WF1 between the sensing element 704 and the electrode Y(1) and the other for waveform WF2 between the sensing element 704 and the electrode X(1). The differential amplifier 712 thus acquires phase information for two waveforms simultaneously along iso-potential surfaces TX(1) and TY(1).

In like fashion, the central processing unit 718 operates the switch units 710 and 714 to simultaneously acquire two differential voltages for the waveforms WF1 and WF2 between the sensing element 704 and the electrodes Y(2)/X(2), then Y(3)/X(3), and so on. In this way, the differential amplifier 712 acquires phase information for two waveforms simultaneously along iso-potential surfaces TX(2)/TY(2), then TX(3)/TY(3), etc. This simultaneously acquired phase information from two waveforms WF1 and WF2 is processed by the data acquisition element 716 to provide a position-indicating output. Greater processing efficiencies can therefore be obtained.

B. Signal Amplitude Analysis Using Different Waveforms

Figure 21:
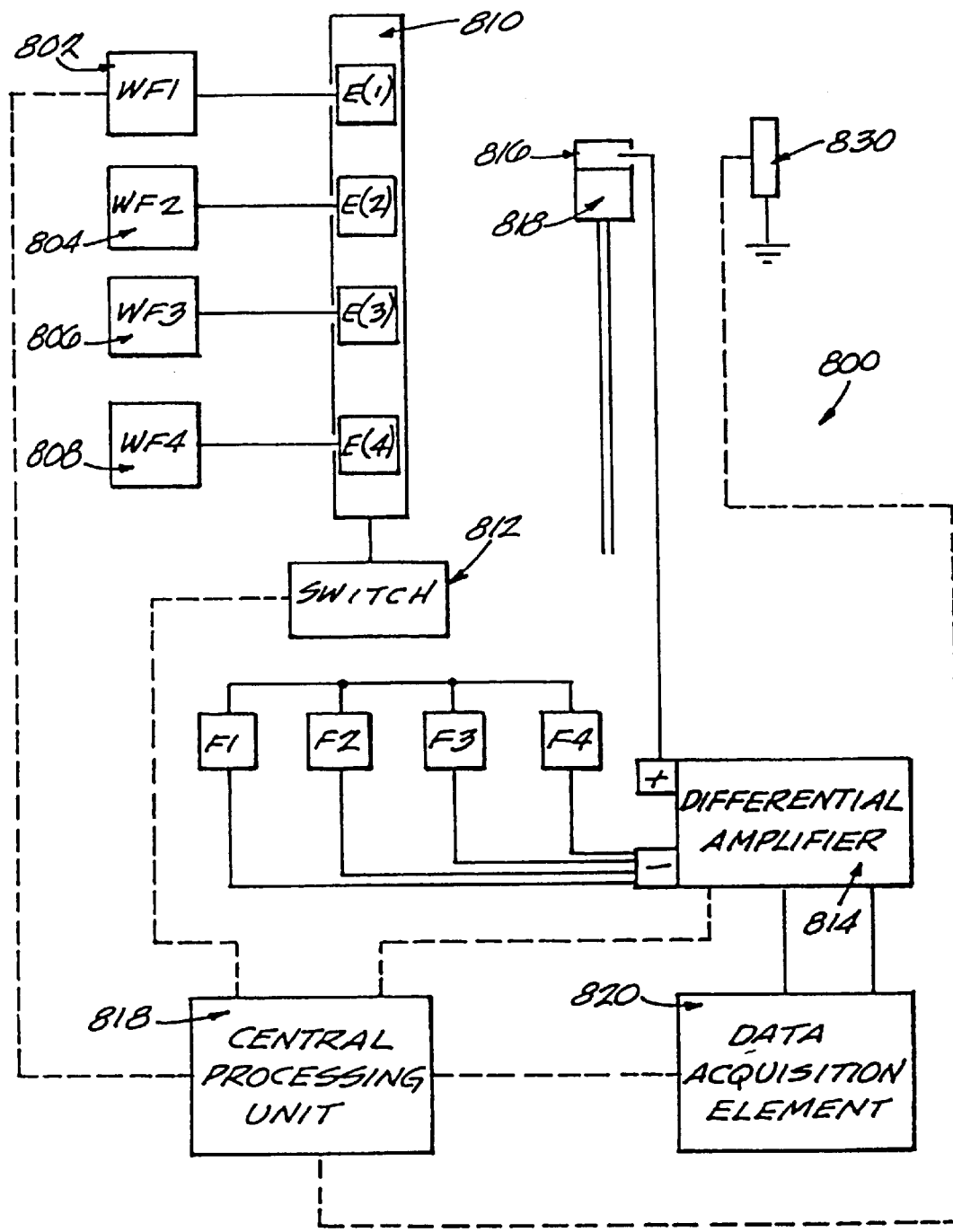
FIG. 21 is a diagrammatic plan view of a system to locate the position of an operative element within a space by generating multiple frequency waveforms from a single locating probe.

FIG. 21 shows a system 800 in which multiple oscillators 802, 804, 806, and 808 apply different waveforms WF1, WF2, WF3, and WF4 simultaneously to multiple electrodes, respectively E(1), E(2), E(3), and E(4), of a single probe 810, through an indifferent return electrode 830. As above described, the different waveforms WF1, WF2, WF3, and WF4 are orthogonal in a signal processing sense possessing, for example, they possess different frequencies. Since the waveforms are applied simultaneously to all electrodes E(1) to E(4), no input switching is required.

All electrodes E(1) to E(4) of the probe 810 are coupled to an output switch 812. The output switch 810 is, in turn, coupled to filters F1, F2, F3, and F4 for the frequencies of, respectively, WF1, WF2, WF3, and WF4. The output of the filters F1, F2, F3, and F4 are coupled to the inverting(−) input of a differential amplifier 814. The sensing element 816 carried by an operative element 818 is coupled to the noninverting (+) input of the differential amplifier 814.

The output of the differential amplifier 814 is coupled to a data acquisition element 820. The data acquisition element 820 includes a rectifier, peak detector, sample and hold element, and analog-to-digital converter coupled as shown in FIG. 3 to process the differential output in the manner previously described, under the control of a central processing unit 818.

Under the control of the central processing unit 818, the data acquisition element 820 simultaneously acquires the differential amplitude of waveform WF1 between the sensing element 816 and the electrode E(1), the differential amplitude of waveform WF2 between the sensing element 816 and the electrode E(2), the differential amplitude of waveform WF3 between the sensing element 816 and the electrode E(3), and the differential amplitude of waveform WF4 between the sensing element 816 and the electrode E(4). As the magnitude of the difference increases as a function of increasing distance between the probe electrodes and the sensing element 816, the data acquisition element 816 is able to simultaneously infer distance with respect to each probe electrode E(1), E(2), E(3), and E(4).

C. Iterative Voltage Analysis Using Multiple Waveforms

Figure 22:
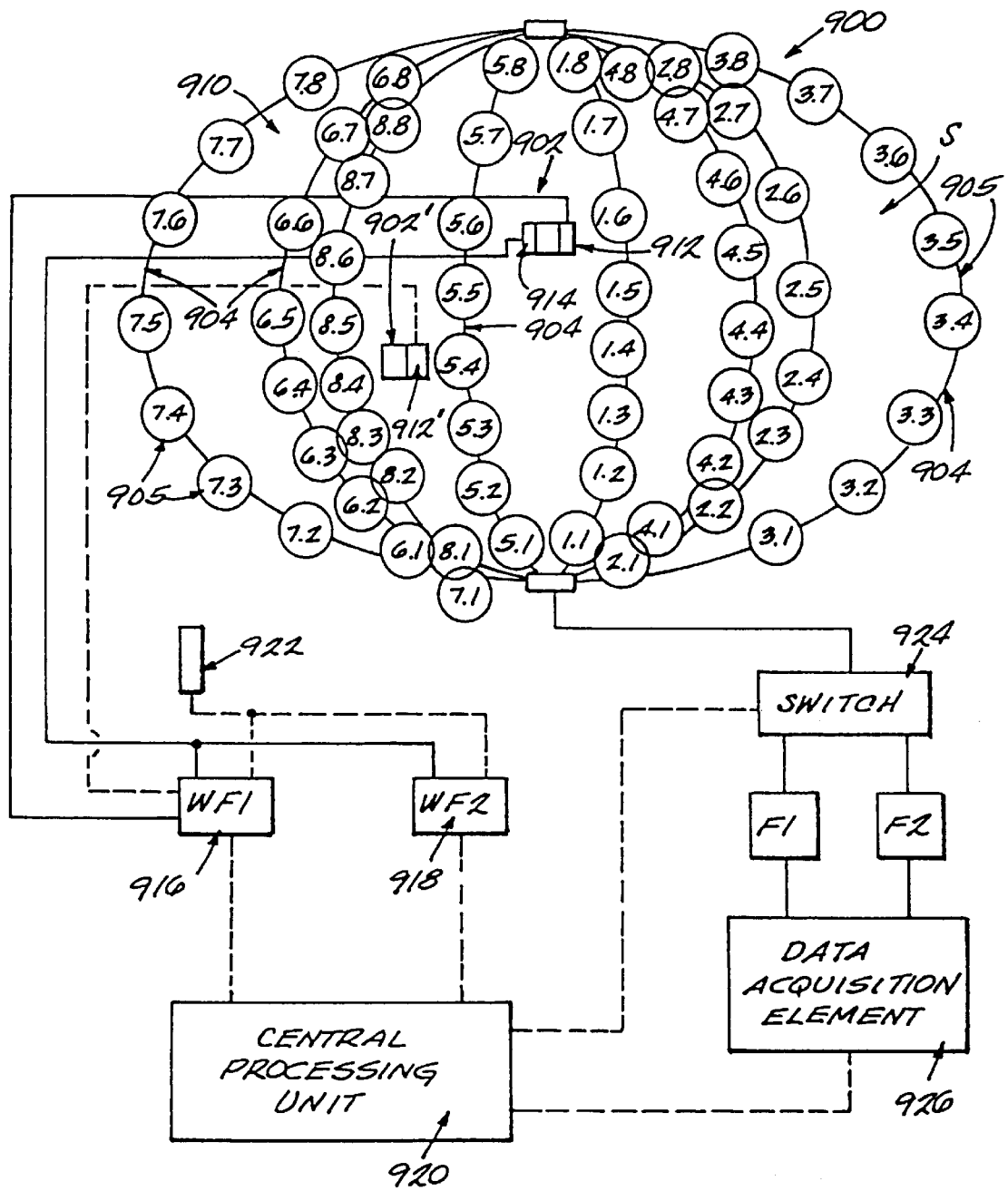
FIG. 22 is a perspective and somewhat diagrammatic view of a composite three-dimensional basket structure of multiple locating probes usable in association an operative element that carries two electrodes for transmitting different frequency waveforms for sensing by the locating probes.

FIG. 22 shows a system 900 for conducting an iterative voltage analysis using multiple waveforms to determine the location of an operative element 902 within a space S peripherally bounded by a composite, three-dimensional basket structure 910, like that shown in FIG. 17.

As in FIG. 17, the composite structure 910 in FIG. 22 includes eight locating probes 904, and each probe, in turn, carries eight electrodes 905, for a total of sixty-four electrodes 905 positioned about the space S. As in FIG. 17, FIG. 22 identifies the electrodes 905 by the designation (A,B), where A=1 to p and B=1 to e, where p is the total number of probes 904 and e is the number of electrodes 905 on each probe 504 (in the illustrated embodiment, p=8 and e=8).

Unlike FIG. 17, the operative element 902 carries two energy transmitting electrodes 912 and 914. Multiple oscillators 916 and 918 apply different waveforms WF1 and WF2 simultaneously to the electrodes 912 and 914. The different waveforms WF1 and WF2 are orthogonal in a signal processing sense possessing, for example, they possess different frequencies. As in FIG. 21, since the waveforms are applied simultaneously to both electrodes 912 and 914, no input switching is required.

In the manner described with respect to the system 500 shown in FIG. 17, a central processing unit 920 conditions the electrode 912 and the electrode 914 to simultaneously transmit waveform energy WF1 and WF2 to a patch return electrode 922. Each probe electrode (A,B) is coupled via a switch 924 to two filters F1 and F2 for the frequencies of the waveforms, respectively, WF1 and WF2. A data acquisition element 926 thereby receives simultaneous inputs from two waveforms WF1 and WF2.

For example, the input for the waveform WF1 could provide a sensed voltage, for use by the algorithm 530 (shown in FIG. 18) in deriving the position-indicating output 528. The input for the waveform WF2 could provide phase and amplitude information for comparison to the phase and amplitude information of waveform WF1, from which the orientation of the operative element 12 can be ascertained. By using multiple waveforms, the system 900 also make possible the derivation of both location and orientation out.

As shown in phantom lines in FIG. 22, a second operative element 902' could be present within the space S bounded by the basket structure 910. The second operative element 902' carries at least one transmitting electrode 912'. Under the control of the central processing unit 920, the electrode 912 of the first operative element 902 transmits the first waveform WF1, while the electrode 912' of the second operative element 902' transmits the second waveform WF2. A data acquisition element 926 thereby receives simultaneous inputs from two waveforms WF1 and WF2, via the filters F1 and F2. The input for the waveform WF1 could provides a sensed voltage, for use by the algorithm 530 (shown in FIG. 18) in deriving the position-indicating output 528 for the first operative element 902, while the input for the waveform WF2 provides a sensed voltage, for use by the algorithm 530 (shown in FIG. 18) in deriving the position-indicating output 528 for the second operative element 902'. Using multiple waveforms, the system 900 is thereby able to provide locating information for multiple operative elements.

With respect to all embodiments in this Specification, which show a data acquisition element coupled by a switch unit to multiple probe electrodes, it should be appreciated that parallel, independent data acquisition channels, each with its own processing components and directly coupled to a single probe electrode, could be substituted.

V. Guiding Multiple Electrode Ablation Arrays

Figure 14:
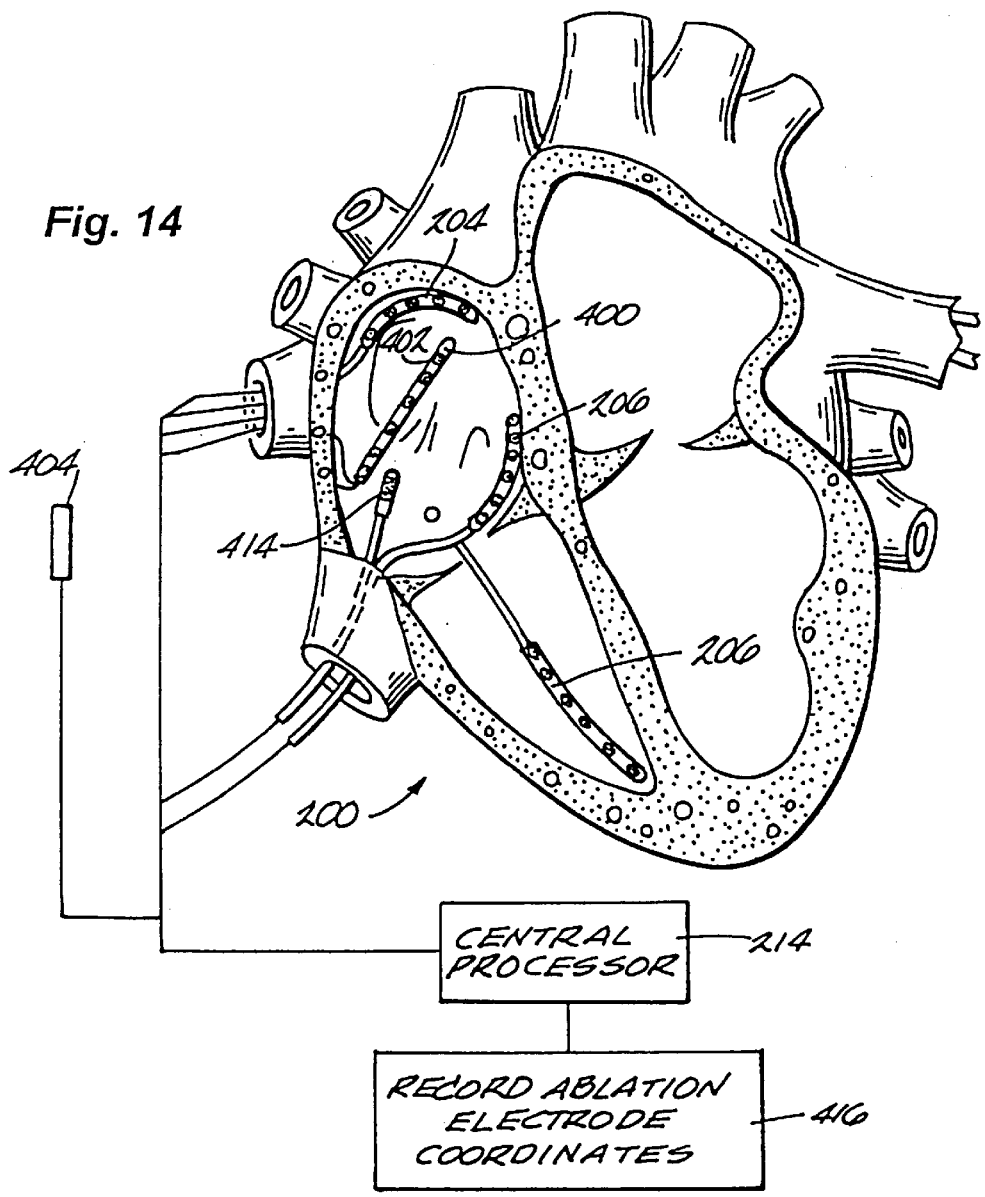
FIG. 14 is a diagrammatic view of a three-dimensional system for locating the position and guiding movement of ablation elements within a heart.

FIG. 14 shows a multiple electrode structure 400 located in the right atrium of a heart. The structure 400 is flexible and carries a steering mechanism (not shown), use of which flexes the structure 400 into curvilinear shapes. The structure 400 carries an array of electrodes 402, which transmit radio frequency energy to ablate myocardial tissue.

The electrodes 402 are preferably operated in a uni-polar mode, in which the radio frequency ablation energy transmitted by the electrodes 402 is returned through an indifferent patch electrode 404 externally attached to the skin of the patient. Alternatively, the electrodes 402 can be operated in a bi-polar mode, in which ablation energy emitted by one or more electrodes 402 is returned an adjacent electrode 402 carried in the structure 400.

Figure 15:
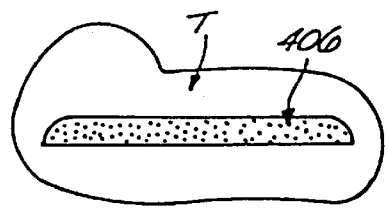
FIG. 15 is a plan view of a representative continuous lesion pattern.

The size and spacing of the electrodes 402 are purposely set for creating continuous, long lesion patterns in tissue, which are capable of treating atrial fibrillation. FIG. 15 shows a representative long, continuous lesion pattern 406 in tissue T. The long continuous lesion pattern 406 is created by additive heating effects between the electrodes 402. The additive heating effects cause the lesion pattern 406 to span adjacent, spaced apart electrodes 402.

Additive heating effects occur either when the spacing between the electrodes 402 is equal to or less than about 3 times the smallest of the diameters of the electrodes 402, or when the spacing between the electrodes 402 is equal to or less than about 2 times the longest of the lengths of the electrodes 402. When the electrodes 402 are spaced in one or both of these manners, the simultaneous application of radio frequency energy by the electrodes 402, in either a bipolar or unipolar mode, creates the elongated continuous lesion pattern 406 typified in FIG. 15.

U.S. patent application Ser. No. 08/566,291, filed Dec. 1, 1995, and entitled "Systems and Methods for Creating Complex Lesion Patterns in Body Tissue" discloses further details regarding systems and methods that create complex long lesion patterns in myocardial tissue. This application is incorporated herein by reference.

Figure 16:
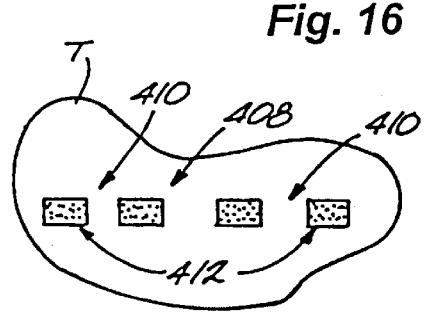
FIG. 16 is a plan view of an representative interrupted lesion pattern.

When the predetermined spacing requirements set forth above are not met, the additive heating effects do not occur, and a segmented, or interrupted, lesion pattern 408 is created. FIG. 16 shows a representative interrupted lesion pattern 408 in tissue T. The interrupted lesion pattern 408 is characterized lesion areas 412 separated by gaps 410 of tissue free of lesions.

An interrupted lesion pattern 408 can also occur, even with proper spacing between electrodes 402, because of insufficient contact between electrodes 402 and tissue, or due to other localized effects not within the immediate control of the physician. After ablation, intracardiac electrogram analysis or intercardiac imaging of the ablation region, or both used in tandem, can be used to uncover the existence of an unintended interrupted lesion pattern 408. In this situation, the physician can deploy an auxiliary ablation electrode 414 (shown in FIG. 14), to ablate tissue in the gaps 410 and thereby complete the desired lesion pattern.

FIG. 14 includes the three-dimensional locating system 200, which was previously described and is shown in greater detail in FIG. 9. Under the control of the central processing unit 214 (previously described), the system 200 locates and helps the physician guide the multiple electrode structure 400 within the right atrium, both before and during the ablation procedure.

In FIG. 14, the central processing unit 214 includes a component 416, which records the location of each ablation electrode 402 when ablating. The position of each electrode 402 is recorded in the same manner as the position of the sensing element 218 of FIG. 9 is derived, using differential comparison of waveform phases between each ablation electrode 402 and the sequentially switched-on transmitting electrodes carried by the locating probes 204, 206, and 208.

When a lesion gap 410 is detected, the system 200 is operated to recall the recorded ablation electrode coordinates from the component 416. From the ablation electrode coordinates, the coordinates of the gap 410 itself can be determined. Knowing the gap coordinates, the system 200 can be used to guide the auxiliary ablation electrode 414 into the gap 410. This feedback, which is preferably updated continuously in real time as the physician moves the auxiliary ablation electrode 414, guides the physician in locating the ablation electrode 414 at the chosen gap ablation site, to thereby complete the desired lesion pattern.

Various features of the invention are set forth in the following claims.

We claim:

1. A system for locating an operative element within an interior body space comprising a locating probe including at least one transmitting element to transmit an electric waveform output within at least a portion of the space, a sensing element adapted to be carried by the operative element to sense a local electric waveform within the space, and a processing element coupled to the sensing element to generate a processed output that locates the sensing element relative to the locating probe based, at least in part, upon a differential comparison of the waveform output and the sensed local waveform.

2. A system for locating an operative element within an interior body space, comprising;

a locating probe including at least one transmitting element to generate an electric waveform in the space, the locating probe carrying a return element comprising a return path for the electric waveform, and a sensing element adapted to be carried by the operative element to sense spatial variations in the electric waveform, wherein the locating probe and sensing element are configured for being coupled to a common processing element.

3. A system for locating an operative element within an interior body space, comprising;

a first locating probe including at least one transmitting element to generate a first electric waveform in the space, the first locating probe including a return path for the first electric waveform, a second locating probe including at least one transmitting element to generate a second electric waveform in the space that, at least in part, intersects the first electric waveform, the second locating probe including a return path for the second electric waveform, a sensing element adapted to be carried by the operative element to sense spatial variations in the intersecting first and second electric waveforms, wherein the first locating probe, second locating probe and sensing element are configured to be coupled to a common processing element.

4. A system according to claim 3 and further including a processing element coupled to the at least one transmitting elements of the first and second locating probes and the sensing element to generate a position-indicating output that locates the sensing element relative to the first and second locating probes based, at least in part, upon analysis of the sensed spatial variations.

5. A system according to claim 3, wherein the first and second probes are in a spaced apart unattached condition.

6. A system according to claim 3, wherein the sensing element includes a first and a second electrode.

7. A system according to claim 6, further including a processing element coupled to the at least one transmitting elements of the first and second locating probes and the sensing element to generate a position-indicating output that locates the first electrode relative to the first and second locating probes based, at least in part, upon analysis of the sensed spatial variations and that derives an orientation-indicating output for the operative element based, at least in part, upon electrical sensing by the second electrode.

8. A system for locating an operative element within an interior body space comprising a locating probe including at least one transmitting element to generate an electric waveform in the space and at least one element spaced from the at least one transmitting element comprising a return path for the electric waveform, a sensing element adapted to be carried by the operative element to sense phase of the electric waveform within the space, and a processing element coupled to the at least one transmitting element and the sensing element to generate a position-indicating output that locates the sensing element in the space relative to the locating probe based upon analysis of the sensed phase.

9. A system for locating an operative element within an interior body space, comprising:

a first and second locating probes each including at least one transmitting element to generate, respectively, first and second electric waveforms in the space and at least one element spaced from the at least one transmitting element comprising a return path for the electric waveform, a sensing element adapted to be carried by the operative element to sense phase of the electric waveform within the space, and a processing element coupled to the at least one transmitting element of each of the respective first and second locating probes and the sensing element to generate a position-indicating output that locates the sensing element in the space relative to the respective first and second locating probes based upon analysis of the sensed phase.

* * * * *